(12) United States Patent
Zhang et al.

(10) Patent No.: US 12,070,607 B2
(45) Date of Patent: *Aug. 27, 2024

(54) METHOD AND APPARATUS FOR CLINICAL EFFECTS-BASED TARGETING OF NEUROSTIMULATION

(71) Applicant: Boston Scientific Neuromodulation Corporation, Valencia, CA (US)

(72) Inventors: Tianhe Zhang, Studio City, CA (US); Michael A. Moffitt, Solon, OH (US); Richard Mustakos, Simi Valley, CA (US); Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/975,468

(22) Filed: Oct. 27, 2022

(65) Prior Publication Data

US 2023/0045684 A1 Feb. 9, 2023

Related U.S. Application Data

(63) Continuation of application No. 17/137,907, filed on Dec. 30, 2020, now Pat. No. 11,517,755, which is a (Continued)

(51) Int. Cl.
*A61N 1/37* (2006.01)
*A61B 5/00* (2006.01)
(Continued)

(52) U.S. Cl.
CPC ........ *A61N 1/37241* (2013.01); *A61B 5/4836* (2013.01); *A61B 5/6868* (2013.01);
(Continued)

(58) Field of Classification Search
CPC ............ A61N 1/37241; A61N 1/36135; A61N 1/36146
See application file for complete search history.

(56) References Cited

U.S. PATENT DOCUMENTS 9,364,665 B2 * 6/2016 Bokil .................. A61N 1/36
10,905,887 B2 * 2/2021 Zhang ................. A61N 1/025
(Continued)

FOREIGN PATENT DOCUMENTS

| CN | 110461410 A | 11/2019 |
|---|---|---|
| WO | WO-2014036075 A1 | 3/2014 |
| WO | WO-2018182881 A1 | 10/2018 |

OTHER PUBLICATIONS

"U.S. Appl. No. 15/902,163, 312 Amendment filed Dec. 18, 2020", 8 pgs.

(Continued)

*Primary Examiner* — Eric D. Bertram
(74) *Attorney, Agent, or Firm* — Schwegman Lundberg & Woessner, P.A.

(57) ABSTRACT

An example of a system for delivering neurostimulation may include a programming control circuit and a stimulation control circuit. The programming control circuit may be configured to generate stimulation parameters controlling delivery of the neurostimulation according to a stimulation configuration. The stimulation control circuit may be configured to specify the stimulation configuration, and may include volume definition circuitry and stimulation configuration circuitry. The volume definition circuitry may be configured to determine one or more test volumes, determine a clinical effect resulting from the one or more test volumes each being activated by the neurostimulation, and determine a target volume using the determined clinical effect. The stimulation configuration circuitry may be con- (Continued)

figured to generate the specified stimulation configuration for activating the target volume.

20 Claims, 17 Drawing Sheets

Related U.S. Application Data continuation of application No. 15/902,163, filed on Feb. 22, 2018, now Pat. No. 10,905,887.

(60) Provisional application No. 62/476,952, filed on Mar. 27, 2017.

(51) Int. Cl.

| | | |
|---|---|---|
| *A61N 1/02* | (2006.01) | |
| *A61N 1/36* | (2006.01) | |
| *A61N 1/372* | (2006.01) | |
| *G16H 20/40* | (2018.01) | |
| *A61B 5/24* | (2021.01) | |
| *A61N 1/05* | (2006.01) | |

(52) U.S. Cl.
CPC .......... *A61N 1/025* (2013.01); *A61N 1/3605* (2013.01); *A61N 1/36125* (2013.01); *A61N 1/36128* (2013.01); *A61N 1/36132* (2013.01); *A61N 1/36135* (2013.01); *A61N 1/36139* (2013.01); *A61N 1/36146* (2013.01); *A61N 1/36185* (2013.01); *G16H 20/40* (2018.01); *A61B 5/24* (2021.01); *A61B 5/7435* (2013.01); *A61N 1/0534* (2013.01)

(56) References Cited

U.S. PATENT DOCUMENTS

| | | | |
|---|---|---|---|
| 2009/0287271 A1 | 11/2009 | Blum et al. | |
| 2012/0296396 A1 | 11/2012 | Moffitt et al. | |
| 2012/0302912 A1* | 11/2012 | Moffitt ................. | A61N 1/3615 607/59 |
| 2016/0030749 A1* | 2/2016 | Carcieri ................. | G16H 50/20 607/45 |
| 2016/0030750 A1* | 2/2016 | Bokil .................... | G16H 50/50 607/45 |
| 2016/0250476 A1* | 9/2016 | Kaemmerer ......... | A61N 1/3614 607/45 |
| 2016/0287889 A1* | 10/2016 | Bokil ................... | A61N 1/0534 |
| 2016/0310743 A1 | 10/2016 | Carcieri et al. | |
| 2017/0080234 A1* | 3/2017 | Gillespie ............ | A61N 1/37247 |
| 2018/0272142 A1 | 9/2018 | Zhang et al. | |
| 2021/0113844 A1 | 4/2021 | Zhang et al. | |

OTHER PUBLICATIONS

"U.S. Appl. No. 15/902,163, Advisory Action dated Jul. 15, 2020", 3 pgs.
"U.S. Appl. No. 15/902,163, Examiner Interview Summary dated Jun. 30, 2020", 3 pgs.
"U.S. Appl. No. 15/902,163, Final Office Action dated May 20, 2020", 8 pgs.
"U.S. Appl. No. 15/902,163, Non Final Office Action dated Jan. 17, 2020", 7 pgs.
"U.S. Appl. No. 15/902,163, Notice of Allowance dated Sep. 24, 2020", 5 pgs.
"U.S. Appl. No. 15/902,163, Response filed Apr. 14, 2020 to Non Final Office Action dated Jan. 17, 2020", 10 pgs.
"U.S. Appl. No. 15/902,163, Response filed Jul. 6, 2020 to Final Office Action dated May 20, 2020", 13 pgs.
"U.S. Appl. No. 15/902,163, Response filed Nov. 19, 2019 to Restriction Requirement dated Oct. 23, 2019", 8 pgs.
"U.S. Appl. No. 15/902, 163, Restriction Requirement dated Oct. 23, 2019", 7 pgs.
"U.S. Appl. No. 17/137,907, Non Final Office Action dated Jun. 6, 2022", 7 pgs.
"U.S. Appl. No. 17/137,907, Notice of Allowance dated Aug. 3, 2022", 8 pgs.
"U.S. Appl. No. 17/137,907, Response filed Jul. 18, 2022 to Non Final Office Action dated Jun. 6, 2022", 9 pgs.
"Australian Application Serial No. 2018244080, First Examination Report dated Feb. 28, 2020", 3 pgs.
"Australian Application Serial No. 2018244080, Response filed Sep. 30, 2020 to First Examination Report dated Feb. 28, 2020", 21 pgs.
"European Application Serial No. 18709851.2, Response to Communication Pursuant to Rules 161 and 162 filed May 12, 2020", 17 pgs.
"International Application Serial No. PCT/US2018/019111, International Preliminary Report on Patentability dated Oct. 10, 2019", 7 pgs.
"International Application Serial No. PCT/US2018/019111, International Search Report dated May 15, 2018", 4 pgs.
"International Application Serial No. PCT/US2018/019111, Written Opinion dated May 15, 2018", 5 pgs.
"Chinese Application Serial No. 201880022353.8, Office Action dated Nov. 18, 2022", w/ English Translation, 18 pgs.
"European Application Serial No. 23185295.5, Extended European Search Report mailed Nov. 20, 2023", 8 pgs.

* cited by examiner

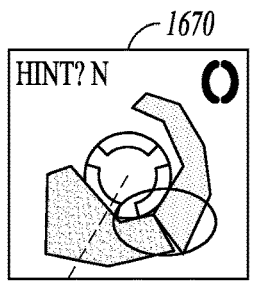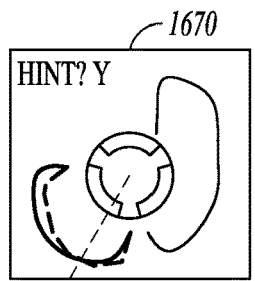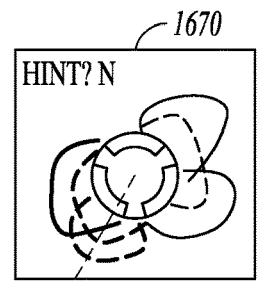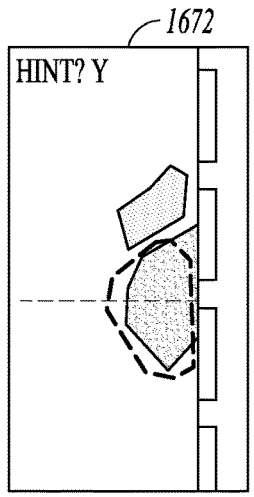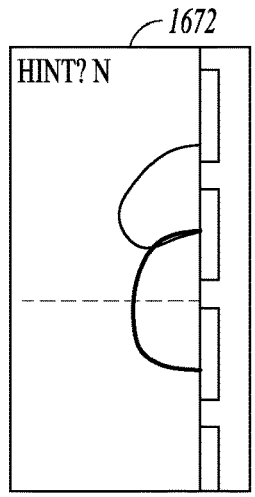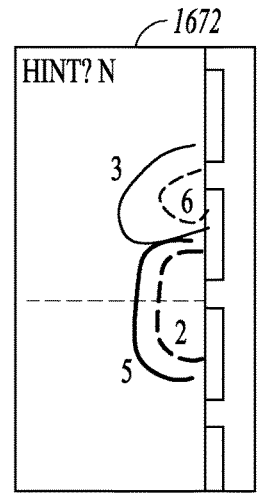
FIG. 18          FIG. 19          FIG. 20
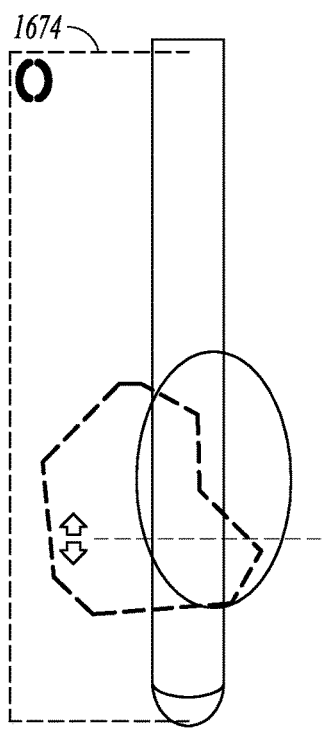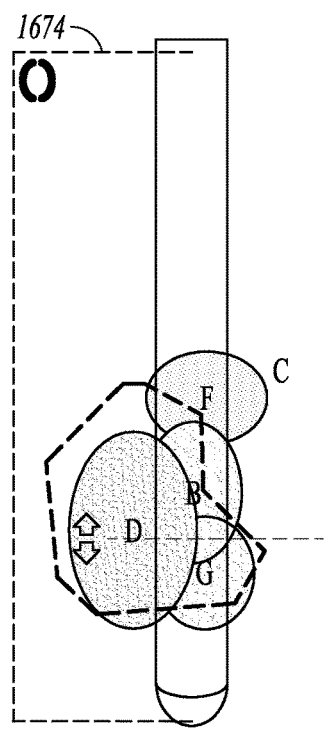
FIG. 21          FIG. 22

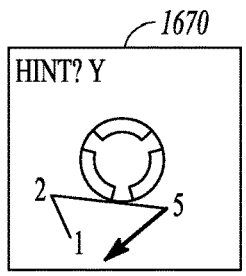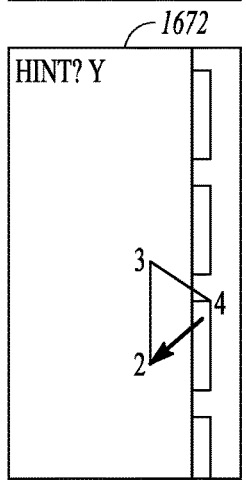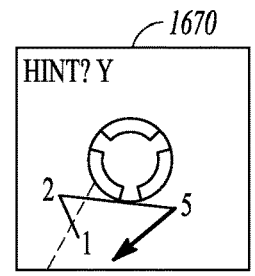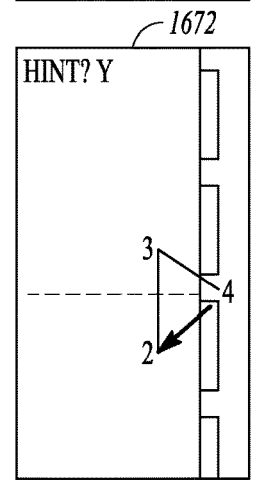
FIG. 25　　　　　　　　FIG. 26
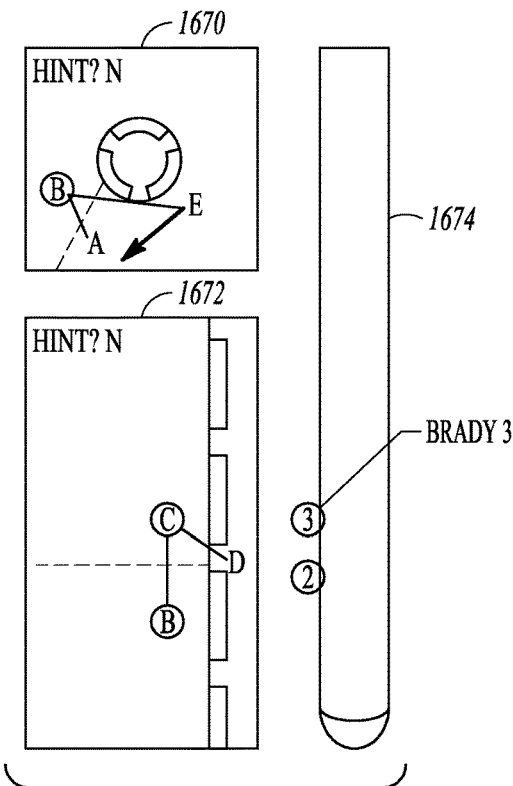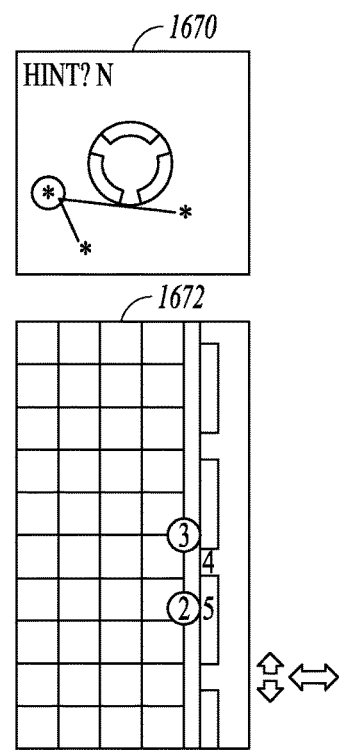
FIG. 27　　　　　　　　FIG. 28

METHOD AND APPARATUS FOR CLINICAL EFFECTS-BASED TARGETING OF NEUROSTIMULATION

CLAIM OF PRIORITY

This application is a continuation of U.S. application Ser. No. 17/137,907, filed Dec. 30, 2020, now U.S. Pat. No. 11,517,755, which is a continuation of U.S. application Ser. No. 15/902,163, filed Feb. 22, 2018, now U.S. Pat. No. 10,905,887, which claims the benefit of priority under 35 U.S.C. § 119(e) of U.S. Provisional Patent Application Ser. No. 62/476,952, filed on Mar. 27, 2017, each of which is herein incorporated by reference in its entirety.

TECHNICAL FIELD

This document relates generally to medical devices and more particularly to a system for programming a stimulation device for neuromodulation using one or more clinical effects.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. The human nervous systems use neural signals having sophisticated patterns to communicate various types of information, including sensations of pain, pressure, temperature, etc. It may interpret an artificial stimulation with a simple pattern of stimuli as an unnatural phenomenon, and respond with an unintended and undesirable sensation and/or movement. Also, as the condition of the patient may change while receiving a neurostimulation therapy, the pattern of neurostimulation pulses applied to the patient may need to be changed to maintain efficacy of the therapy while minimizing the unintended and undesirable sensation and/or movement. While modern electronics can accommodate the need for generating sophisticated pulse patterns that emulate natural patterns of neural signals observed in the human body, the capability of a neurostimulation system depends on its post-manufacturing programmability to a great extent. For example, a sophisticated pulse pattern may only benefit a patient when it is customized for that patient and updated timely in response to changes in the patient's conditions and needs. This makes programming of a stimulation device for a patient a challenging task.

SUMMARY

An example (e.g., "Example 1") of a system for delivering neurostimulation to tissue of a patient using a plurality of electrodes and controlling the delivery of the neurostimulation by a user is provided. The system may include a programming control circuit and a stimulation control circuit. The programming control circuit may be configured to generate a plurality of stimulation parameters controlling delivery of the neurostimulation according to a stimulation configuration. The neurostimulation is delivered through one or more electrodes of the plurality of electrodes. The stimulation control circuit may be configured to specify the stimulation configuration, and may include volume definition circuitry and stimulation configuration circuitry. The volume definition circuitry may be configured to determine one or more test volumes, determine a clinical effect resulting from the one or more test volumes each being activated by the neurostimulation, and determine a target volume using the determined clinical effect. The one or more test volumes and the target volume each represent a portion of the tissue. The stimulation configuration circuitry may be configured to generate the specified stimulation configuration for activating the target volume.

In Example 2, the subject matter of Example 1 may optionally be configured such that the one or more test volumes comprises a plurality of test volumes, and the volume definition circuitry is further configured to determine the plurality of test volumes, determine clinical effect information sets each representing the clinical effect resulting from activation of a test volume of the determined plurality of test volumes by the neurostimulation, and determine the target volume using the clinical effect information sets.

In Example 3, the subject matter of Example 2 may optionally be configured such that the volume definition circuitry is further configured to allow the user to mark a test volume of the plurality of test volumes as a mark volume to allow for tracking of attempts of determining the target volume.

In Example 4, the subject matter of any one or a combination of Examples 2 and 3 may optionally be configured such that the volume definition circuitry is further configured to automatically generate a recommended volume using one or more clinical effect information sets of the determined clinical effect information sets.

In Example 5, the subject matter of Example 4 may optionally be configured such that the volume definition circuitry is further configured to allow the user to set the target volume to the mark volume, the recommended volume, or a test volume of the plurality of test volumes.

In Example 6, the subject matter of Example 5 may optionally be configured to further include a display screen and a user input device, and such that the volume definition circuitry is further configured to present one or more of the target volume, the mark volume, the recommended volume, the plurality of test volumes, or one or more graphical representation of one or more clinical effect information sets of the determined clinical effect information sets on the display screen in one or more of a cross-sectional view at a cross-section selected by the user using the user input device or a perspective view at a perspective angle selected by the user using the user input device, and the stimulation configuration circuitry is further configured to present a graphical representation of the stimulation configuration in a stimulation configuration panel on the display screen.

In Example 7, the subject matter of any one or a combination of Examples 2 to 6 may optionally be configured such that the stimulation configuration circuitry is further configured to allow the user to specify test stimulation configurations, and the volume definition circuitry is further configured to determine the plurality of test volumes each being a volume of the tissue to be activated by delivery of the neurostimulation according to a test stimulation configuration of the test stimulation configurations.

In Example 8, the subject matter of any one or a combination of Examples 2 to 7 may optionally be configured such that the volume definition circuitry is further configured to determine the clinical effect information sets based on information entered by one or more of the patient or the user.

In Example 9, the subject matter of any one or a combination of Examples 2 to 8 may optionally be configured such that the volume definition circuitry is further configured to determine the clinical effect information sets automatically using signals sensed from the patient.

In Example 10, the subject matter of any one or a combination of Examples 2 to 9 may optionally be configured such that the volume definition circuitry is further configured to determine the clinical effect information sets including a measure of a therapeutic benefit and a measure of a side effect.

In Example 11, the subject matter of Example 10 may optionally be configured such that the volume definition circuitry is further configured to determine a therapeutic benefits contour indicative of a volume of the tissue excitable for one or more desirable therapeutic benefits and a side effect contour indicative of a volume of the tissue excitable for one or more unwanted side effects.

In Example 12, the subject matter of any one or a combination of Examples 1 to 11 may optionally be configured such that the stimulation configuration circuitry is configured to generate the stimulation configuration automatically by executing an inverse modeling algorithm using a stimulation field model (SFM) relating the stimulation configuration to the stimulation volume.

In Example 13, the subject matter of Example 12 may optionally be configured such that the stimulation configuration circuitry is configured to generate the stimulation configuration using a library including data mapping stimulation volumes to stimulation configurations.

In Example 14, the subject matter of Example 12 may optionally be configured such that the stimulation configuration circuitry is configured to generate the stimulation configuration using an analytical derivation of the stimulation configuration from the stimulation volume.

In Example 15, the subject matter of any one or a combination of Examples 1 to 14 may optionally be configured such that the stimulation configuration circuitry is configured to determine an electrode configuration of the stimulation configuration. The electrode configuration specifies a selection of one or more electrodes from the plurality of electrodes and a fractionalization of electrical current flowing through the selected one or more electrodes.

An example (e.g., "Example 16") of a method for controlling delivery of neurostimulation to tissue of a patient using a plurality of electrodes is also provided. The method may include specifying one or more test volumes each representing a portion of the tissue, determining a clinical effect resulting from the one or more test volumes each being activated by the neurostimulation, determining a target volume using the determined clinical effect, the target volume representing another portion of the tissue, determining a stimulation configuration using the target volume, and generating a plurality of stimulation parameters for controlling delivery of the neurostimulation through one or more electrodes of the plurality of electrodes according to the stimulation configuration.

In Example 17, the subject matter of determining the stimulation configuration as found in Example 16 may optionally include determining an electrode configuration specifying a selection of the one or more electrodes from the plurality of electrodes and a fractionalization of electrical current flowing through the selected one or more electrodes.

In Example 18, the subject matter of determining the stimulation configuration as found in any one or a combination of Examples 16 and 17 may optionally include generating the stimulation configuration automatically using a library including data mapping stimulation volumes to stimulation configurations.

In Example 19, the subject matter of determining the stimulation configuration as found in any one or a combination of Examples 16 and 17 may optionally include generating the stimulation configuration automatically using an analytical derivation of the stimulation configuration from the stimulation volume.

In Example 20, the subject matter the one or more test volumes as found in any one or a combination of Examples 16 to 19 may optionally include a plurality of test volumes, and the subject matter determining the target volume as found in any one or a combination of Examples 16 to 19 may optionally include specifying the plurality of test volumes, determining clinical effect information sets each resulting from activation of a test volume of the plurality of test volumes by the neurostimulation, and determining the target volume using the determined clinical effect information sets.

In Example 21, the subject matter of determining the target volume as found in Example 20 may optionally further include allowing a user to mark a test volume of the plurality of test volumes as a mark volume to allow for tracking of attempts of determining the target volume.

In Example 22, the subject matter of determining the target volume as found in Example 21 may optionally further include automatically generating a recommended volume using one or more clinical effect information sets of the determined clinical effect information sets.

In Example 23, the subject matter of determining the target volume as found in Example 22 may optionally further include allowing the user to set the target volume to the mark volume, the recommended volume, or a test volume of the plurality of test volumes.

In Example 24, the subject matter of any one or a combination of Examples 22 and 23 may optionally further include presenting one or more of the target volume, the mark volume, the recommended volume, the plurality of test volumes, or one or more graphical representation of one or more clinical effect information sets of the clinical effect information sets on a display screen in one or more of a cross-sectional view at a cross-section selected by the user or a perspective view at a perspective angle selected by the user, and presenting a graphical representation of the stimulation configuration on the display screen.

In Example 25, the subject matter of presenting the one or more graphical representation of the one or more clinical effect information sets as found in Example 24 may optionally include determining and presenting a therapeutic benefits contour indicative of a volume of the tissue excitable for one or more desirable therapeutic benefits, and determining and presenting a side effect contour indicative of a volume of the tissue excitable for one or more unwanted side effects.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 18 illustrates an example of cross-sectional view of target volumes and clinical effects on a user interface, such as the user interface of FIG. 9.

FIG. 19 illustrates another example of cross-sectional view of target volumes and clinical effects on a user interface, such as the user interface of FIG. 9.

FIG. 20 illustrates another example of cross-sectional view of target volumes and clinical effects on a user interface, such as the user interface of FIG. 9.

FIG. 21 illustrates an example of perspective view of target volumes and clinical effects on a user interface, such as the user interface of FIG. 9.

FIG. 22 illustrates another example of perspective view of target volumes and clinical effects on a user interface, such as the user interface of FIG. 9.

FIG. 25 illustrates another example of presenting a recommended volume and clinical effects on a user interface, such as the user interface of FIG. 9.

FIG. 26 illustrates an example of presenting a mark and clinical effects on a user interface, such as the user interface of FIG. 9.

FIG. 27 illustrates another example of presenting a mark and clinical effects on a user interface, such as the user interface of FIG. 9.

FIG. 28 illustrates another example of presenting a mark and clinical effects on a user interface, such as the user interface of FIG. 9.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system allowing for configuration of settings for a stimulation device and/or lead to deliver therapeutic stimulation using the results of manual and/or automated clinical effect and side effect mapping. In various embodiments, the neuromodulation system can include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device. While DBS is discussed as a specific example, the present subject matter can also be applied to program stimulation devices for delivering various types of neuromodulation therapies.

In various embodiments, the neurostimulation system can allow target volumes of stimulation to be defined and refined by clinical effect mapping, provide guidance to a clinician on optimized program settings based on existing clinical effect maps, algorithm-generated guidance, and/or marked positions, and/or automatically configure stimulation settings (e.g., electrode polarities and fractionalizations), pulse amplitudes, and/or pulse widths from the target volumes. In various embodiments, the neuromodulation system can include a user interface through which a user can perform volume definition and stimulation targeting.

Figure 1:
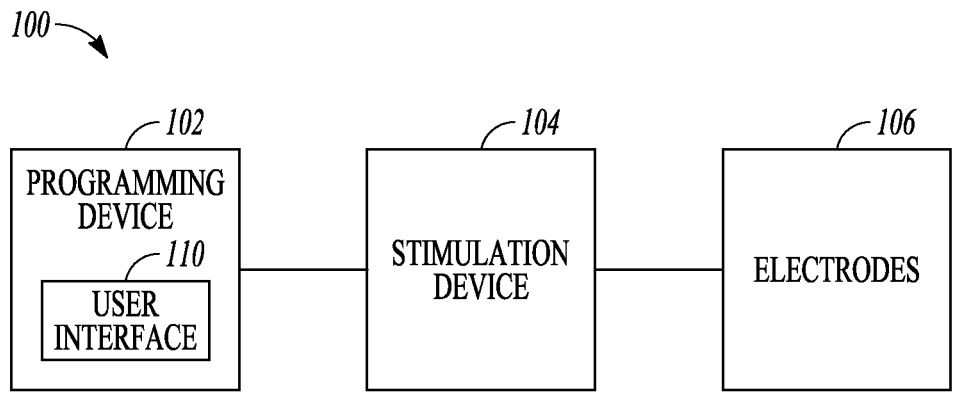
FIG. 1 illustrates an embodiment of a neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100; a "patient" includes a person who receives or is intended to receive neurostimulation delivered using system 100. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for DBS applications. Such DBS configuration includes various features that may simplify the task of the user in programming stimulation device 104 for delivering DBS to the patient, such as the features discussed in this document.

Figure 2:
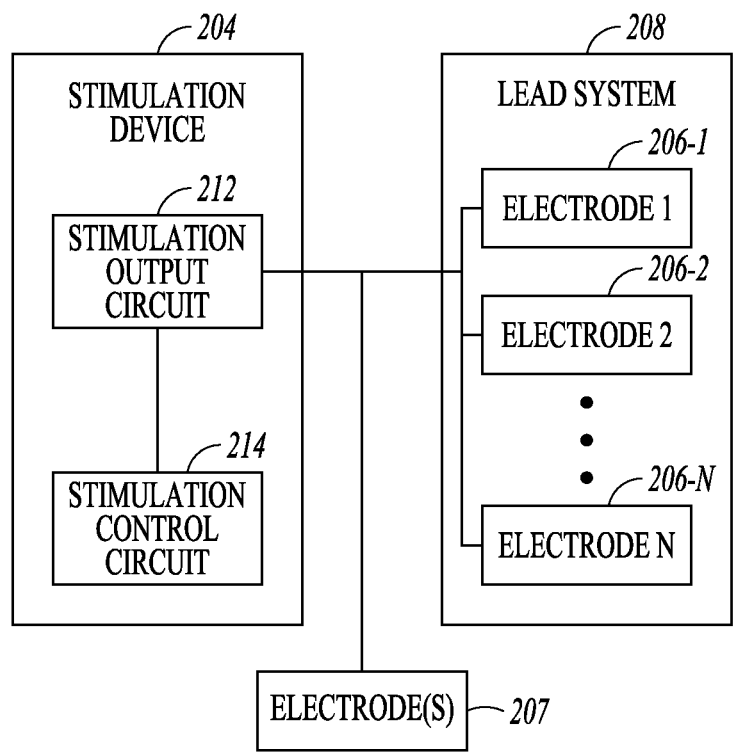
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where $N \geq 2$. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
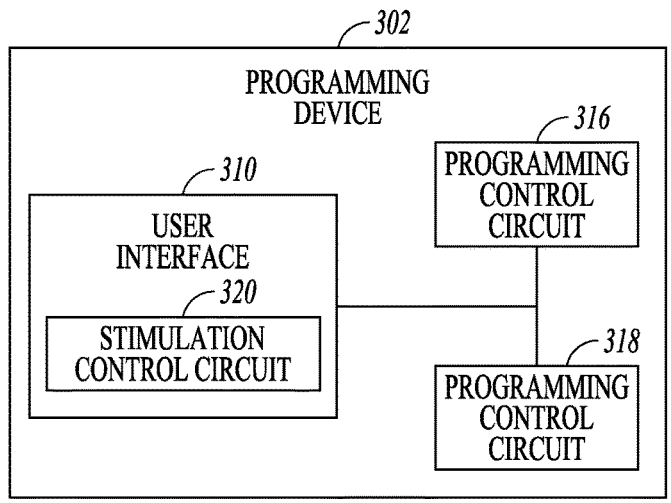
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface 310. Programming control circuit 316 generates the plurality of stimulation parameters that controls the delivery of the neurostimulation pulses according to a specified stimulation configuration that can define, for example, stimulation waveform and electrode configuration. User interface 310 represents an embodiment of user interface 110 and includes a stimulation control circuit 320. Storage device 318 stores information used by programming control circuit 316 and stimulation control circuit 320, such as information about a stimulation device that relates the stimulation configuration to the plurality of stimulation parameters and information relating the stimulation configuration to a volume of activation in the patient. In various embodiments, stimulation control circuit 320 can be configured to support one or more functions allowing for programming of stimulation devices, such as stimulation device 104 including its various embodiments as discussed in this document, using an assessment of clinical effects, as further discussed below with reference to FIGS. 9-29.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "stimulation configuration" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
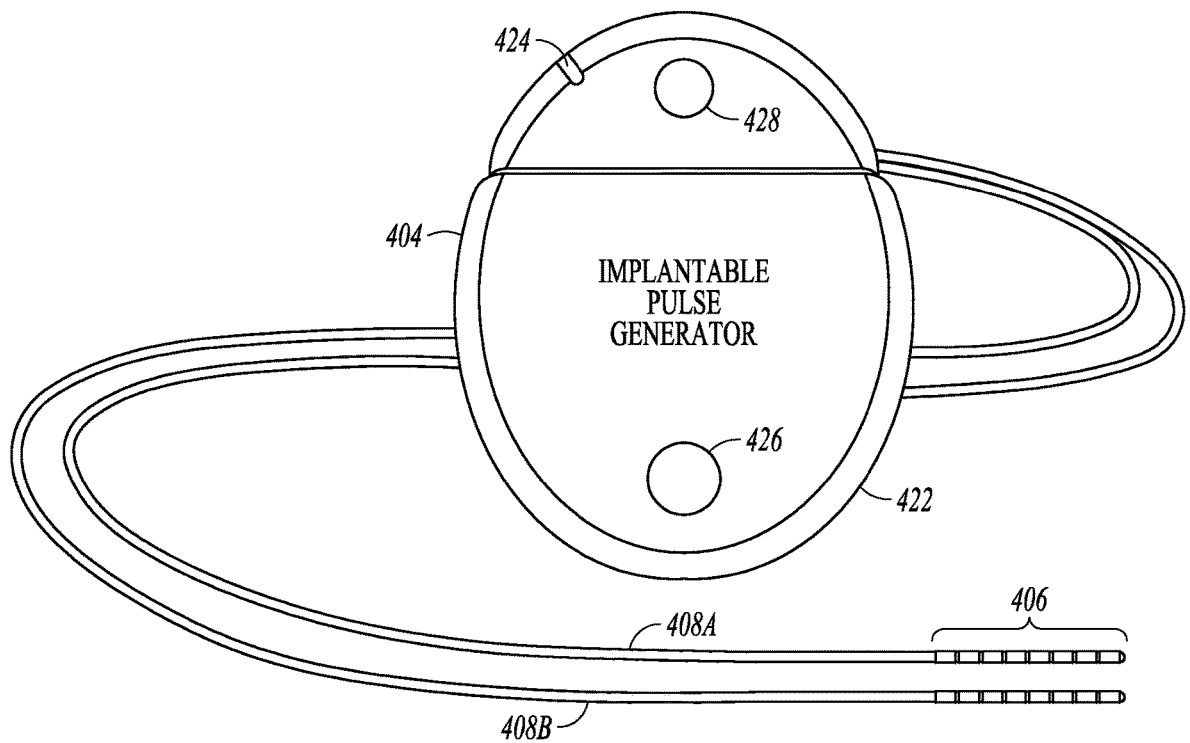
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain, or configured to provide electrical neurostimulation energy to a nerve cell target included in the subject's spinal cord.

Figure 5:
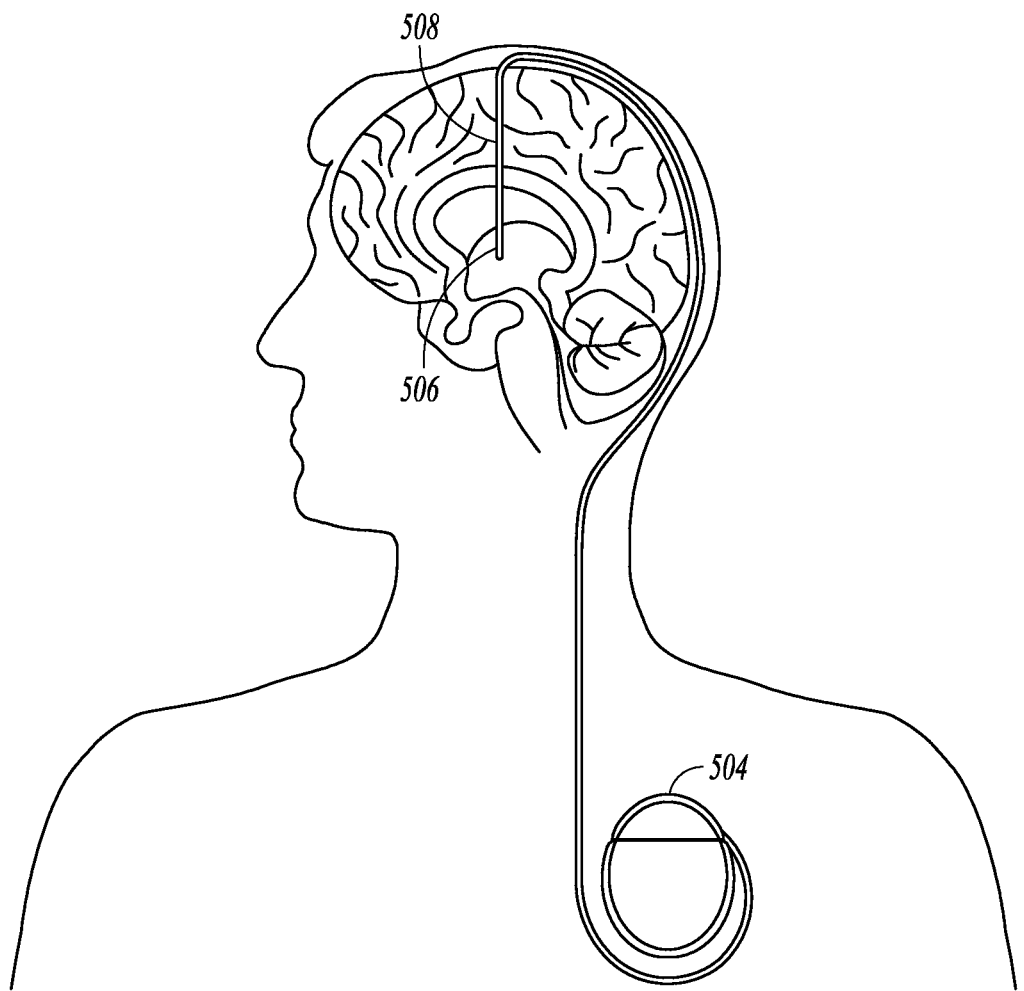
FIG. 5 illustrates an embodiment of an IPG and an implantable lead system, such as the IPG and lead system of FIG. 4, arranged to provide neurostimulation to a patient.

FIG. 5 illustrates an embodiment of an IPG 504 and an implantable lead system 508 arranged to provide neurostimulation to a patient. An example of IPG 504 includes IPG 404. An example of lead system 508 includes one or more of leads 408A and 408B. In the illustrated embodiment, implantable lead system 508 is arranged to provide Deep Brain Stimulation (DBS) to a patient, with the stimulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), cortex, globus pallidus externus (GPe), medial forebrain bundle (MFB), periaquaductal gray (PAG), periventricular gray (PVG), habenula, subgenual cingulate, ventral intermediate nucleus (VIM), anterior nucleus (AN), other nuclei of the thalamus, zona incerta, ventral capsule, ventral striatum, nucleus accumbens, and any white matter tracts connecting these and other structures.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
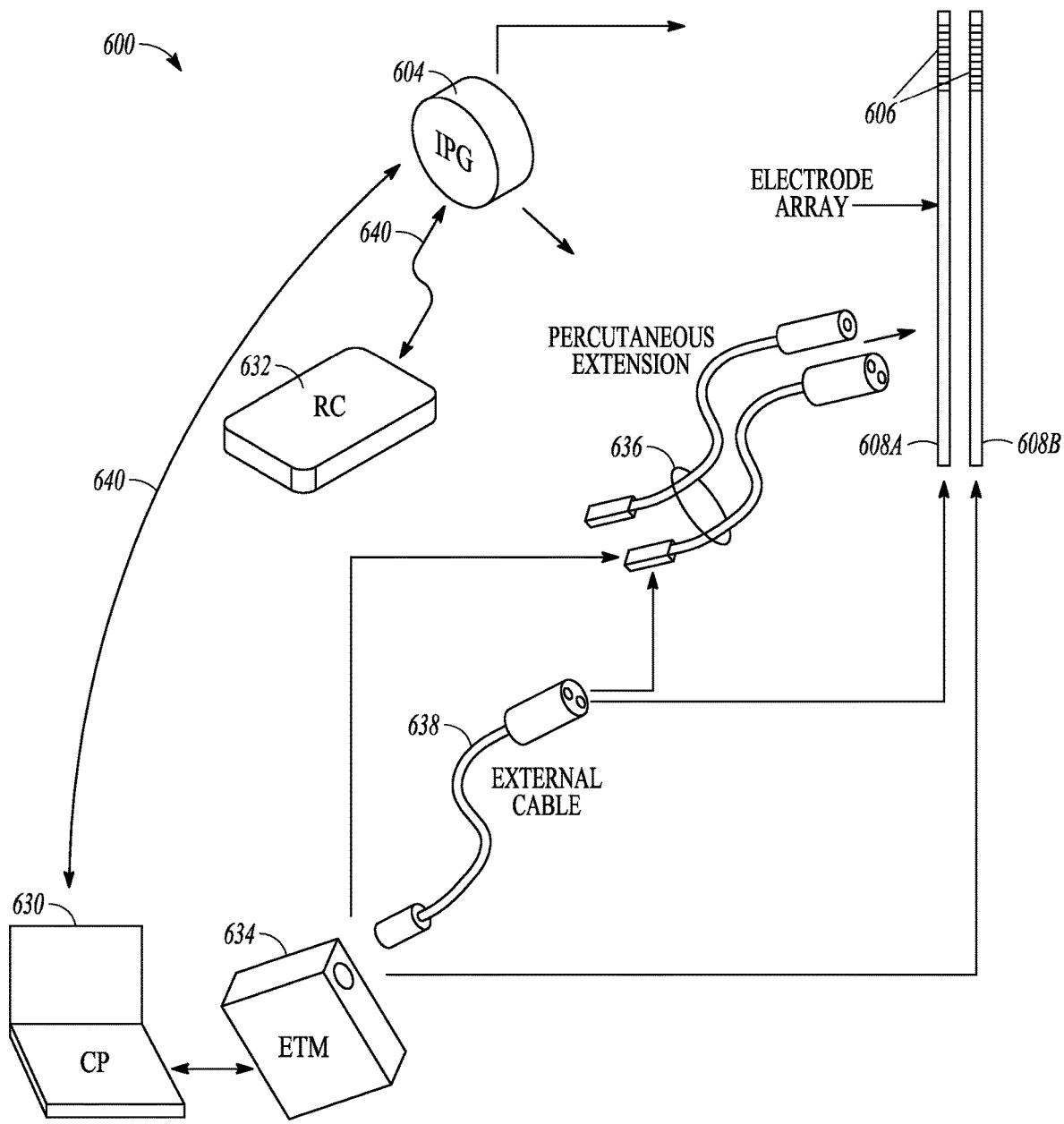
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial modulator (ETM) 634. IPG 404 may be electrically coupled to leads 608A and 608B directly or through percutaneous extension leads 636. ETM 634 may be electrically connectable to leads 608A and 608B via one or both of percutaneous extension leads 636 and/or external cable 638. System 600 represents an embodiment of system 100, with IPG 604 representing an embodiment of stimulation device 104, electrodes 606 of leads 608A and 608B representing electrodes 106, and CP 630, RC 632, and ETM 634 collectively representing programming device 102.

ETM 634 may be standalone or incorporated into CP 630. ETM 634 may have similar pulse generation circuitry as IPG 604 to deliver neurostimulation energy according to specified modulation parameters as discussed above. ETM 634 is an external device that is typically used as a preliminary stimulator after leads 408A and 4083 have been implanted and used prior to stimulation with IPG 604 to test the patient's responsiveness to the stimulation that is to be provided by IPG 604. Because ETM 634 is external it may be more easily configurable than IPG 604.

CP 630 can configure the neurostimulation provided by ETM 634. If ETM 634 is not integrated into CP 630, CP 630 may communicate with ETM 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$, is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments. CP 630 is able to program RC 632 when remotely located from RC 632.

Figure 7:
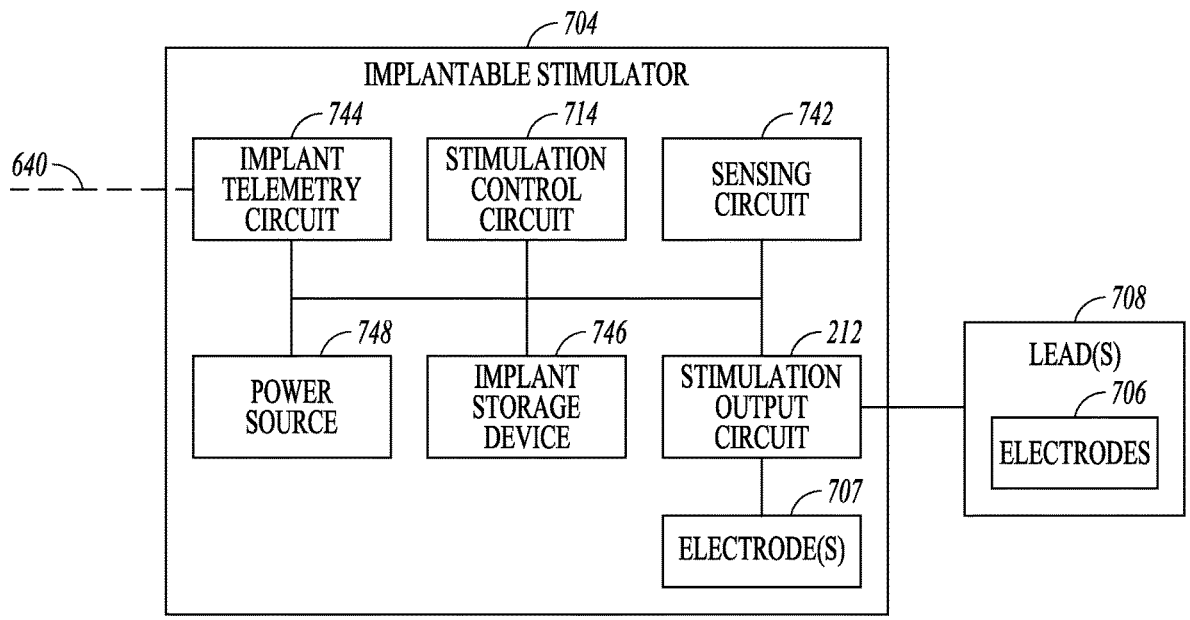
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an embodiment of stimulation device 104 or 204 and may be implemented, for example, as IPG 604. Lead(s) 708 represents an embodiment of lead system 208 and may be implemented, for example, as implantable leads 608A and 608B. Lead(s) 708 includes electrodes 706, which represents an embodiment of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707, and delivers each of the neurostimulation pulses through a set of electrodes selected from electrodes 706 and electrode(s) 707. Stimulation control circuit 714 represents an embodiment of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 stores values of the plurality of stimulation parameters. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640, and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
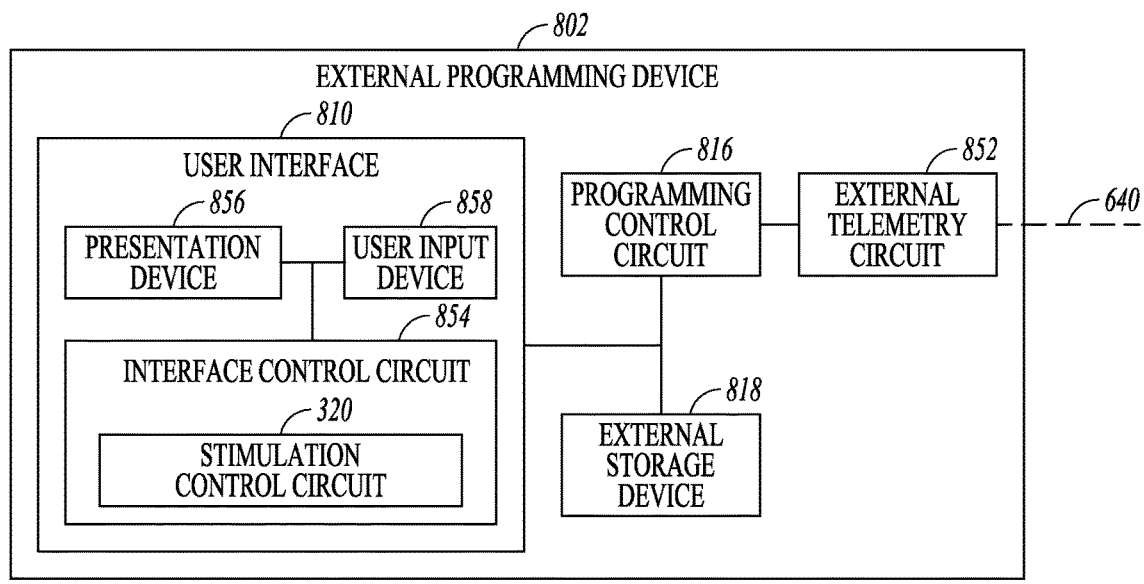
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an embodiment of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an embodiment of programming control circuit 316 and generates the plurality of stimulation parameters, which is to be transmitted to implantable stimulator 704, based on a specified stimulation configuration (e.g., the pattern of neurostimulation pulses as represented by one or more stimulation waveforms and one or more stimulation fields, or at least certain aspects of the pattern). The stimulation configuration may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an embodiment of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms, and transmits the plurality of stimulation parameters with the updated values to implantable stimulator 704.

Figure 9:
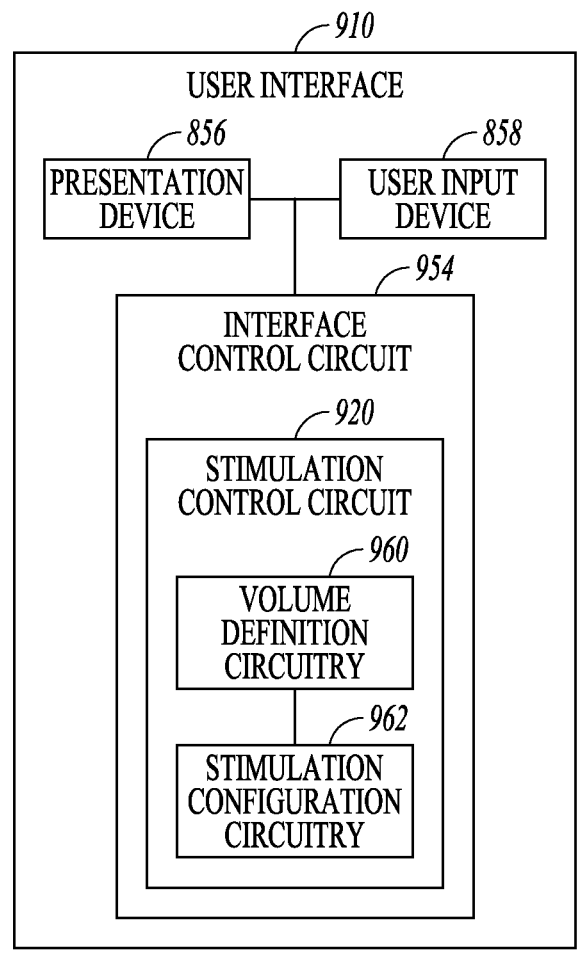
FIG. 9 illustrates an embodiment of a user interface of an external programming device, such as the external programming device of FIG. 8.

FIG. 9 illustrates an embodiment of a user interface 910 of an external programming device, such as external programming device 803. User interface 910 represents an embodiment of user interface 810 and allows the user to define the stimulation configuration and perform various other monitoring and programming tasks. User interface 910 includes display screen 856, user input device 858, and an interface control circuit 954. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 910 includes a GUI that allows the user to perform any functions discussed in this document where graphical presentation and/or editing are suitable as may be appreciated by those skilled in the art.

Interface control circuit 954 represents an embodiment of interface control circuit 854 and includes a stimulation control circuit 920, which represents an embodiment of stimulation control circuit 320 and specifies the stimulation configuration. Stimulation control circuit 920 includes volume definition circuitry 960 and stimulation configuration circuitry 962. Volume definition circuitry 960 can be configured to determine a target volume using one or more clinical effects resulting from activation of one or more test volumes by neurostimulation (e.g., delivery of the neurostimulation pulses as discussed in this document). Stimulation configuration circuitry 962 can be configured to allow the user to enter or select one or more stimulation configurations each corresponding to a test volume, and configured to generate a stimulation configuration based on the target volume. In this document, a "target volume" refers to a volume of activation for which a medical device such as implantable stimulator 704 is programmed to deliver a neurostimulation therapy to treat the patient, and a "test volume" refers to a volume of activation used in a process of determining the target volume. In various embodiments, stimulation configuration circuitry 962 can be used to enter and/or generate the stimulation configuration that specifies at least the fractionalization.

In one embodiment, stimulation configuration circuitry 962 generates the stimulation configuration for activating a stimulation volume substantially matching the target volume. The target volume includes a first portion of tissue of the patient. The stimulation volume includes a second portion of the tissue. Ideally, the first portion of the tissue and the second portion of the tissue are the same portion of tissue. In practice, the stimulation volume should substantially match the target volume such that the difference between the first portion of the tissue and the second portion of the tissue is minimized.

Figure 10:
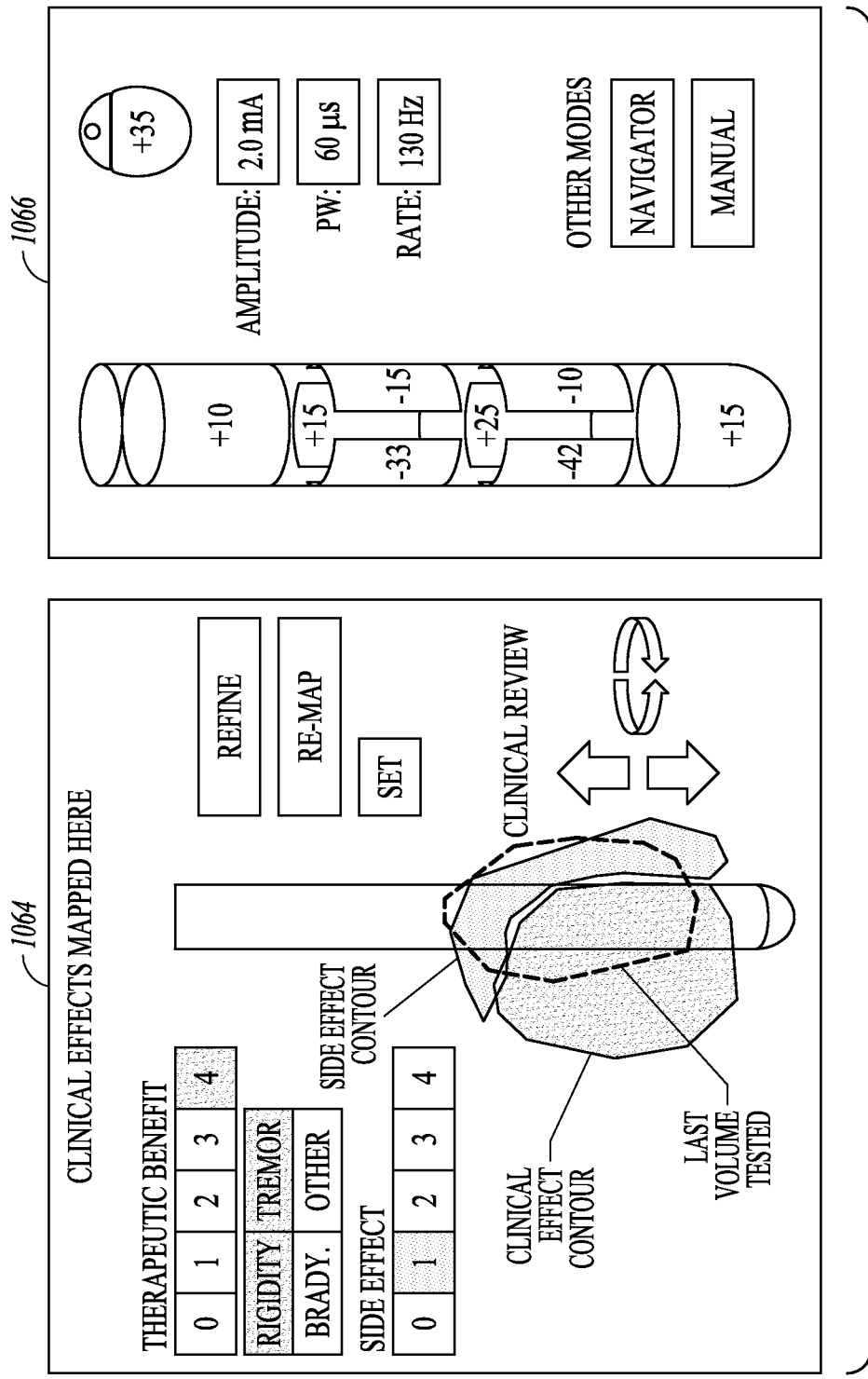
FIG. 10 illustrates an example of a presentation of clinical effects and stimulation configuration on a user interface, such as the user interface of FIG. 9.

FIG. 10 illustrates an example of a presentation of clinical effects and stimulation configuration on user interface 910. Volume definition circuitry 960 can present the target volume and the one or more clinical effects using presentation device 856. Stimulation configuration circuitry 962 can present the stimulation configuration using presentation device 856. In the illustrated example, volume definition circuitry 960 presents the target volume and the one or more clinical effects in a volume definition panel 1064 on a display screen of presentation device 856, and stimulation configuration circuitry 962 presents the stimulation configuration in a stimulation configuration panel 1066 on the display screen. Stimulation configuration panel 1066 shows electrode configuration including polarity and fractionalization, and stimulation pulse parameters including amplitude, width, and frequency. A "Navigator" button can open a navigation console that allows the user to navigate predefined stimulation configurations and select a predefined stimulation configuration. A "Manual" button can open a manual programming console that allows the user to manually define a stimulation configuration.

In various embodiments, determination of the target volume using one or more clinical effects, including generation of various other volumes of activation during the process of determining the target volume, can be independent of the stimulation device and the lead system used. After the target volume is determined, stimulation configuration circuitry 962 can automatically generate the stimulation configuration for activating a volume of tissue substantially matching the target volume. Examples of the various other volume of activations include test volume, mark volume, and recommended volume (also referred to as a "hint"), as further discussed below in this document. Such volumes can each be considered as an attempted target volume used in an iterative process of determining the final target volume.

In various embodiments, stimulation configuration circuitry 962 can execute an inverse modeling algorithm that automatically generates the stimulation configuration for activating a volume of tissue in the patient that substantially matches the target volume. The target volume can be defined and refined by one or more iterations using the one or more clinical effects resulting from the test volume used in each iteration. In various embodiments, the user can specify a test volume for each iteration. For example, stimulation configuration circuitry 962 can receive a stimulation configuration from the user (who manually defines the stimulation configuration or selects one from stored stimulation configurations), and generate a test volume to be result from delivery of neurostimulation using the stimulation configuration. Alternatively, the user can specify a test volume, and stimulation configuration circuitry 962 can execute the inverse modeling algorithm to automatically generate the stimulation configuration for activating that test volume. In one embodiment, the inverse modeling algorithm is based on a stimulation field model (SFM) relating a stimulation configuration to a volume of activation. The stimulation configuration can be generated using a library including data mapping volumes of activation to stimulation configurations and/or using an analytical derivation of the stimulation configuration that generates the stimulation volume.

In various embodiments, volume definition circuitry 960 can determine the one or more clinical effects and/or present the one or more clinical effects using presentation device 856 using information entered by the user, information entered by the patient, and/or signals sensed from the patient. As illustrated in FIG. 10, the clinical effects as presented in volume definition panel 1064 can include those represented by one or more types of therapeutic benefits and one or more types of side effects. A therapeutic benefit score representative of a degree of the one or more therapeutic benefits (0 for no therapeutic benefit, 4 for highest degree of therapeutic benefit), and a side effect score representative of a degree of the one or more side effects (0 for no side effect, 4 for highest degree of side effect), are presented. As illustrated in FIG. 10, the clinical effects as presented in volume definition panel 1064 can further include a therapeutic benefits contour and a side effect contour. The therapeutic benefits contour is indicative of a volume of the tissue excitable for one or more desirable therapeutic benefits. The side effect contour is indicative of a volume of the tissue excitable for one or more unwanted side effects. In various embodiments, volume definition circuitry 960 can present these clinical effects, including the types, scores, and/or contours using presentation device 856, such as in volume definition panel 1064 of the display screen as illustrated in FIG. 10. Stimulation configuration circuitry 962 can present the target volume including any one or more attempted target volumes using presentation device 856, such as the "Last Volume Tested" displayed in volume definition panel 1064 of the display screen as illustrated in FIG. 10.

FIGS. 11-15 each illustrate another example of a presentation of the clinical effects in volume definition panel 1064 and the stimulation configuration in stimulation configuration panel 1066. These examples show the process of determining the target volume using the clinical effects. In one embodiment of the process, volume definition circuitry 960 can (i) determine and/or present one or more test volumes each corresponding to a stimulation configuration, (ii) determine one or more clinical effect sets each resulting from a test volume of the one or more test volumes being activated by the neurostimulation using the corresponding stimulation configuration, (iii) mark a test volume as a mark volume (or "mark") to allow for tracking of the attempts in defining the target volume, (iv) automatically generate a recommended volume (or a "hint") based on one or more test volumes and one or more clinical effect sets associated with the one or more test volumes, and (v) determine the target volume using the one or more clinical effect sets associated with the one or more test volumes, the mark volume(s), and/or the recommended volume(s). The one or more clinical effect sets can each include an overall therapeutic benefit score, one or more therapeutic benefit types, a therapeutic benefit score for each of the one or more therapeutic benefit types, an overall side score, one or more side effect types, a side effect score for each of the one or more side effect types, a therapeutic benefits contour, and/or a side effect contour, each of which can be selectively displayed in volume definition panel 1064. In various embodiments, volume definition circuitry 960 can be configured to perform each of (i)-(v) automatically and/or with input from the user and/or the patient. Stimulation configuration circuitry 962 specifies the stimulation configuration and display the stimulation configuration in stimulation configuration panel 1066. While the neurostimulation including delivery of electrical pulses is discussed as an example, any other forms of neurostimulation can be programmed using the clinical effects according to the present subject matter. In the illustrated examples, the stimulation configuration is specified by pulse parameters and electrode polarity and fractionalization parameters. The stimulation pulse parameters can include pulse amplitude (e.g., in mA), pulse duration (e.g., in μs), and pulse frequency (e.g., in Hz, or inter-pulse interval in μs). Each electrode can be specified as an anode or a cathode, and assigned a fraction of the pulse amplitude. The fraction can be specified as a percentage of the pulse amplitude or specified as an absolute amplitude value.

Figure 11:
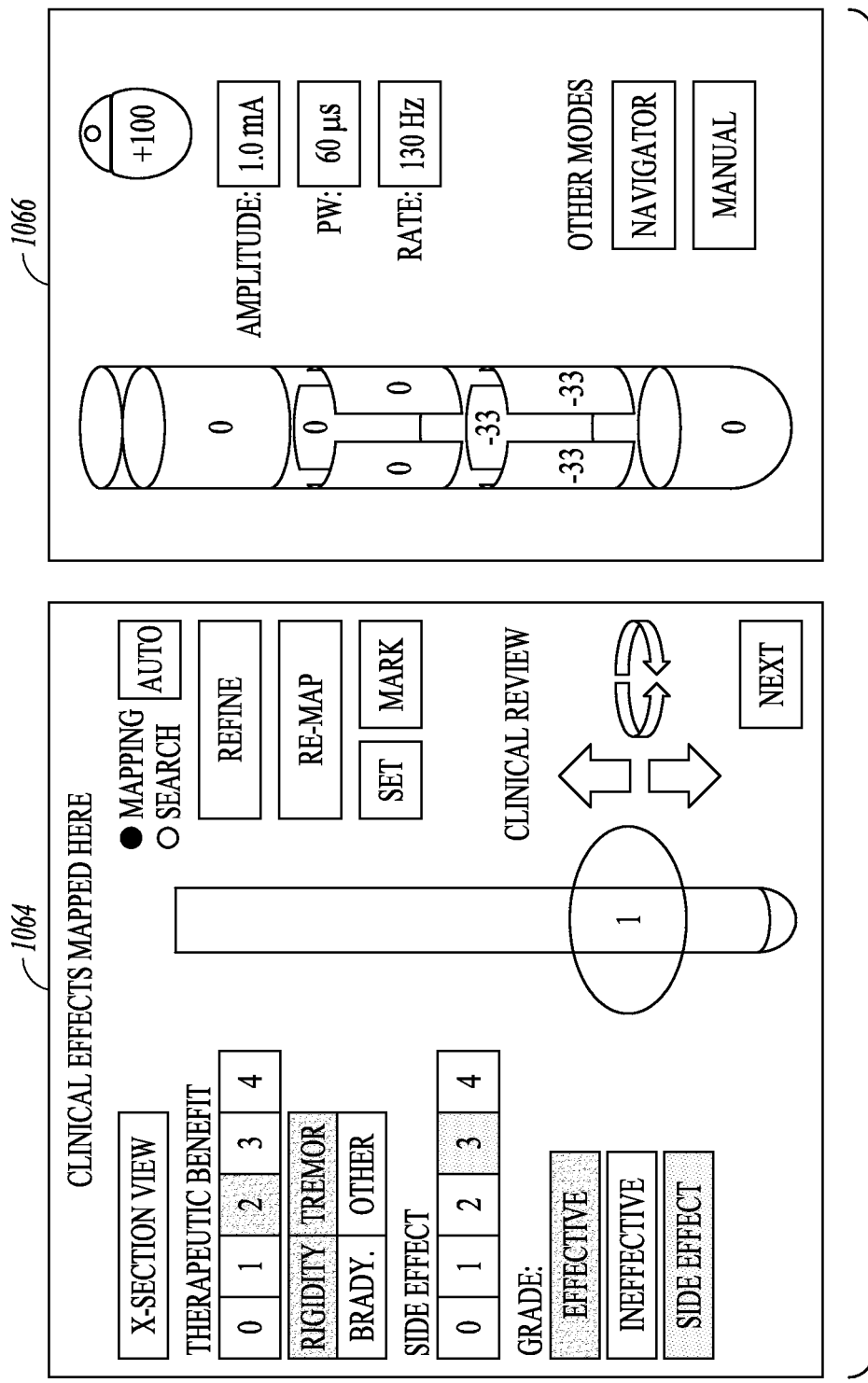
FIG. 11 illustrates another example of a presentation of clinical effects and stimulation configuration on a user interface, such as the user interface of FIG. 9.

FIG. 11 shows that volume definition circuitry 960 has determined a first test volume, determined a first clinical effect set resulting from the first test volume being activated by the neurostimulation, and marked the first test volume as a first mark volume (mark "1"). FIG. 11 shows an example in which an initial (the first) stimulation configuration (e.g., with monopolar electrode configuration as shown) is defined by the user (e.g., manually). After the first test volume is determined, the user can grade the first test volume with clinical effect scores (e.g., the therapeutic benefit score and the side effect score), and a graphical representation of a net effect can be displayed in the volume definition panel 1064 in a 2-dimensional cross-sectional view or a 3-dimensional view of a volume of tissue. This graphical representation of the test volume can be filled with a color and/or labeled with another visual marker (e.g., a star, a mark such as a number, or a colored circle) denoting the clinical effect entry. The graphical representation of the next test volume can be overlaid onto that of the current (and prior) test volumes, and the procedure is repeated until a satisfactory target volume is determined. Clinical effect scores (e.g., the therapeutic benefit score and the side effect score) can span multiple symptoms, and/or multiple symptoms may be represented by distinct clinical effect data structures (e.g., dyskinesia and rigidity), though the data can also be merged into one composite score, which can be represented by a composite color, for example.

Figure 12:
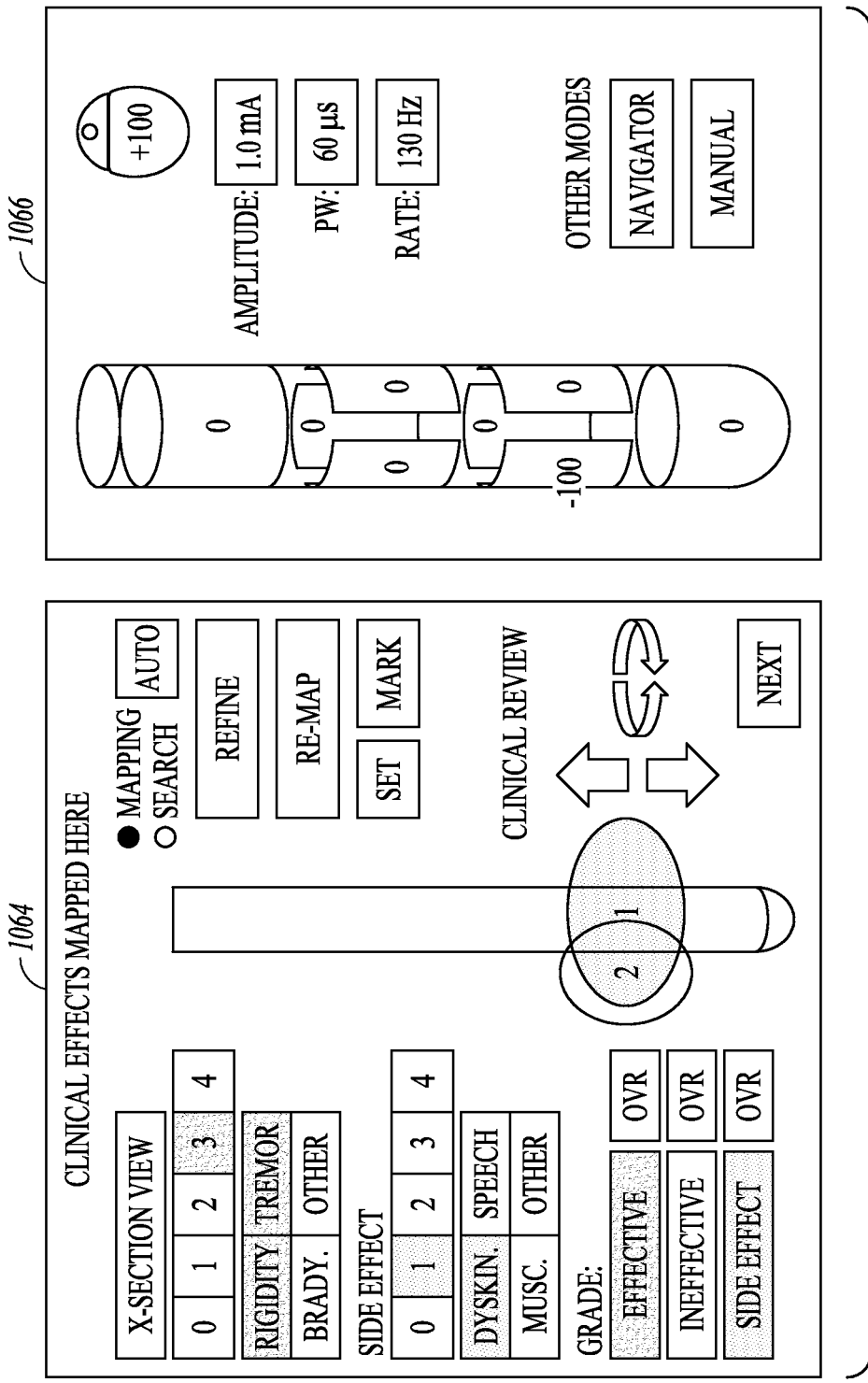
FIG. 12 illustrates another example of a presentation of clinical effects and stimulation configuration on a user interface, such as the user interface of FIG. 9.

FIG. 12 shows that volume definition circuitry 960 has determined a second test volume, determined a second clinical effect set resulting from the second test volume being activated by the neurostimulation, and marked the second test volume as a second mark volume (mark "2").

Figure 13:
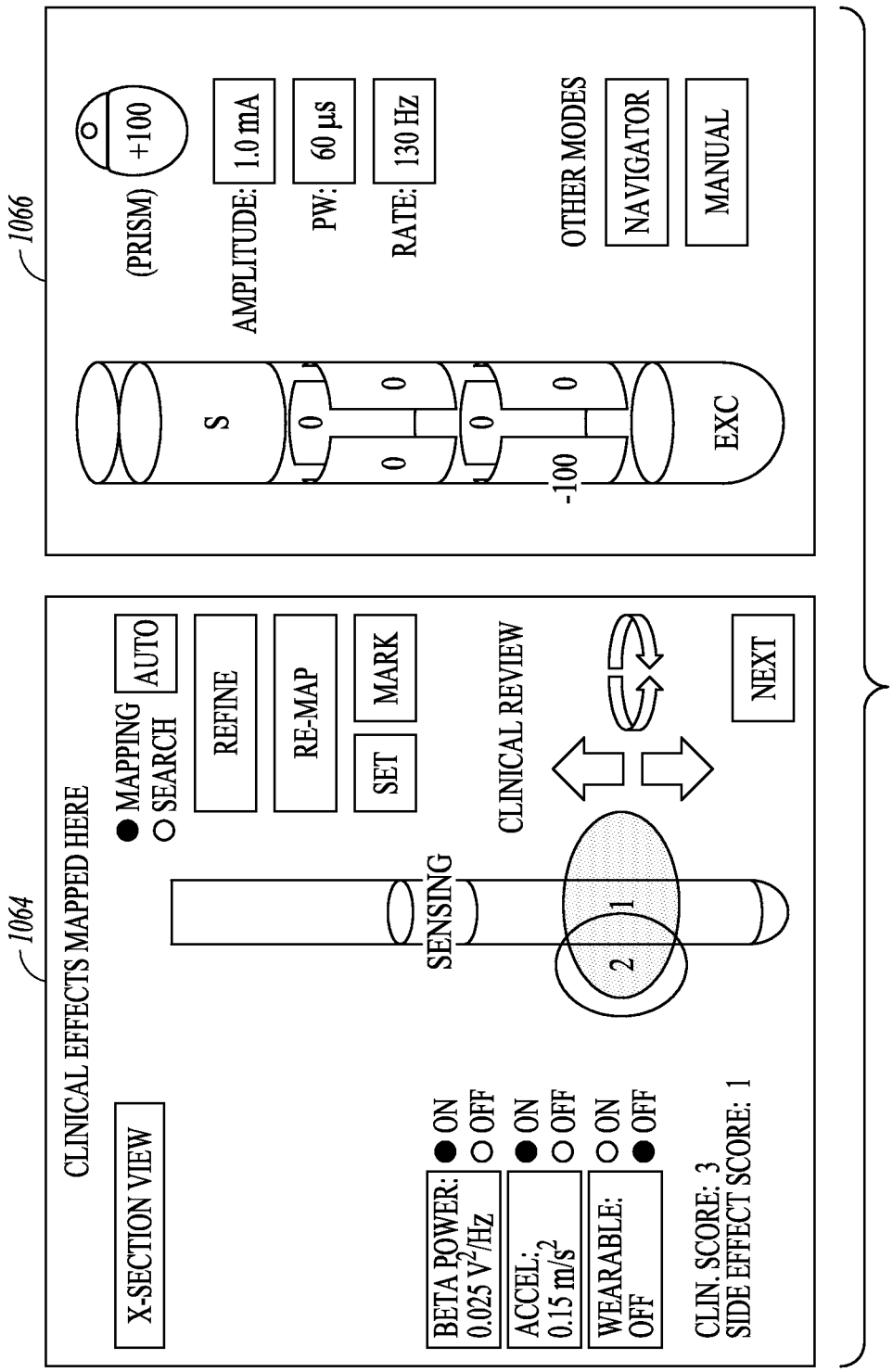
FIG. 13 illustrates another example of a presentation of clinical effects and stimulation configuration on a user interface, such as the user interface of FIG. 9.

As shown in FIG. 13, the clinical effects can include those derived from signals sensed from the patient. In various embodiments, the clinical effects can be entered by be user and/or the patient, and/or derived automatically from measurements using various sensors. The sensors can include wearable and/or implantable sensors that senses signals such as movement signal (acceleration), local field potential signal, electroencephalogram (EEG) signal (e.g., sensed using a wearable sensor), single unit activity signal (e.g., sensed using an implantable sensor), electromyogram (EMG) signal (e.g., for indicating rigidity and/or tremor, sensed using a wearable sensor), a posture signal (e.g., for indicating spinal alignment, sensed using a wearable sensor), dopamine/neurotransmitter level signal (e.g., sensed using an implantable sensor placed in certain nuclei), and/or signal indicative of inflammatory factors or other markers of glial cell activity or death (e.g., sensed using an implantable sensor placed in certain nuclei). Specific measurements can be toggled. One or more indicators each denoting sensing electrode(s) and/or biometric sensor(s) can be displayed in volume definition panel 1064. One or more indicators each denoting sensing electrode(s) can also be displayed in stimulation configuration panel 1066. In stimulation configuration panel 1066, sensing electrodes can be excluded in calculations determining the stimulation configuration, such as by using the manual mode (e.g., tip electrode excluded in the example illustrated in FIG. 13).

Figure 14:
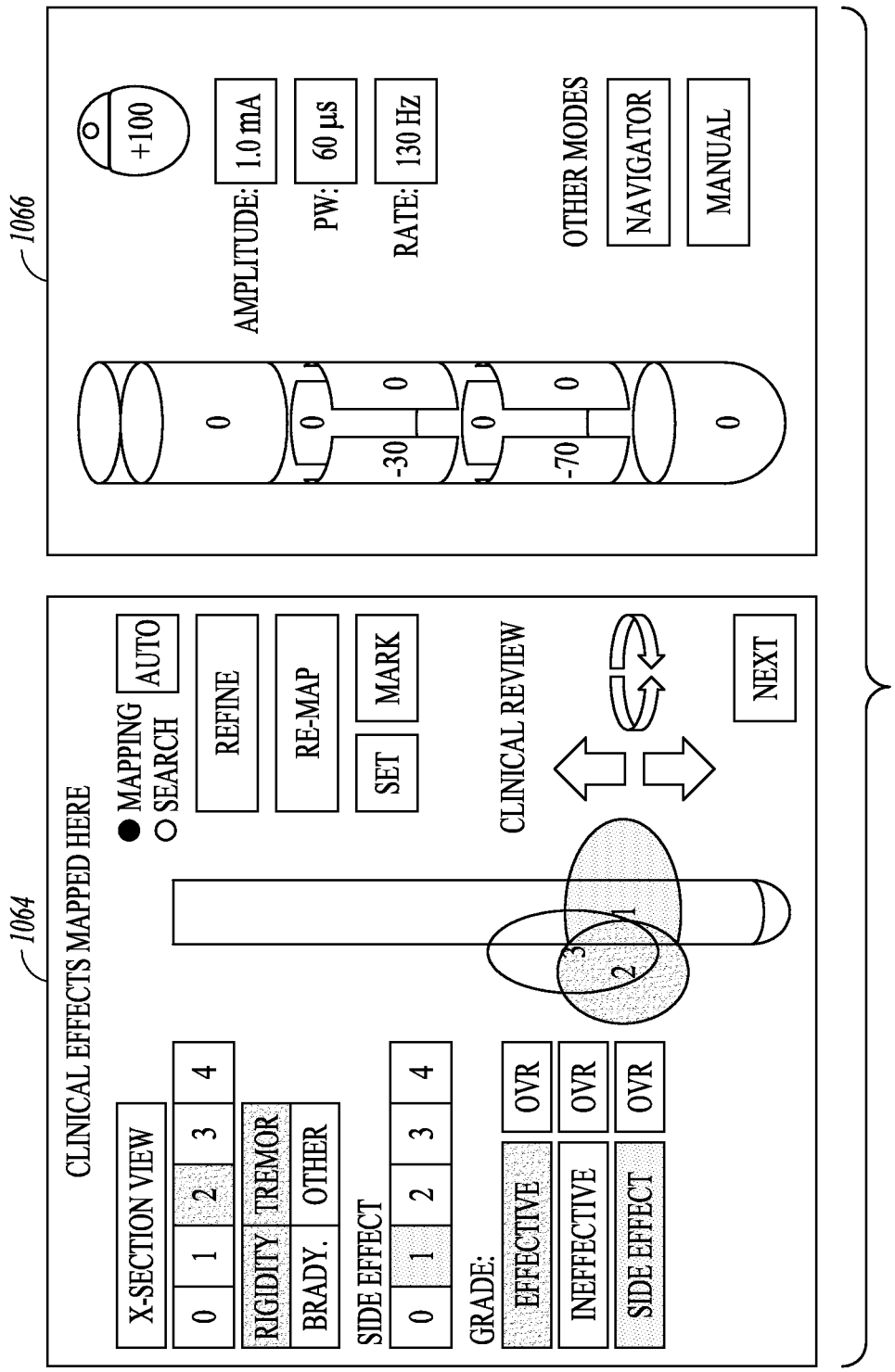
FIG. 14 illustrates another example of a presentation of clinical effects and stimulation configuration on a user interface, such as the user interface of FIG. 9.

FIG. 14 shows that volume definition circuitry 960 has determined a third test volume, determined a third clinical effect set resulting from the third test volume being activated by the neurostimulation, and marked the third test volume as a third mark volume (mark "3"). In various embodiments, test volumes can be "built" in this way through successive iterations. FIGS. 11, 12, and 14 illustrate examples of the presentation of clinical effects and stimulation configuration during the first three iterations in an attempt to determine the target volume. The iterations can follow heuristic rules, for example, in both perspective and cross-sectional views of the volumes. Representation of side effects can default to background. An automated mapping/search button ("Auto") allow the user to toggle to an algorithmic search that automatically sweeps through available stimulation configurations for mapping clinical effects (under a mapping mode, when "Mapping" is selected) or finding an optical stimulation (under a search mode, when "Search" is selected). Different algorithms/search paths are activated depending on whether the clinical effects are mapped or the optimal stimulation is searched.

Figure 15:
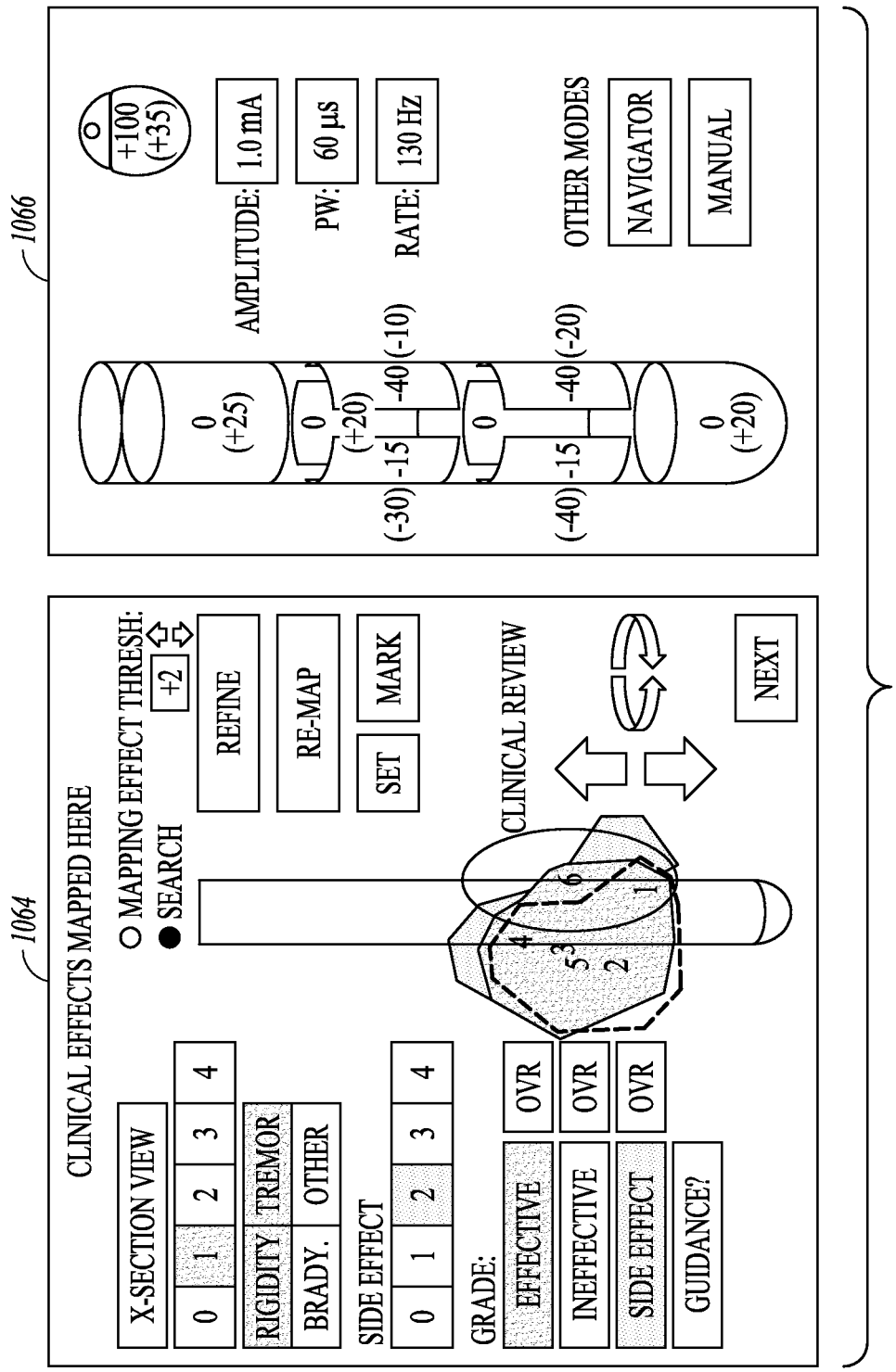
FIG. 15 illustrates another example of a presentation of clinical effects and stimulation configuration on a user interface, such as the user interface of FIG. 9.

FIG. 15 shows that volume definition circuitry 960 has determined three additional test volumes, determined three corresponding additional clinical effect sets resulting from each of the three corresponding additional test volumes activated by the neurostimulation, and marked the corresponding additional test volumes as fourth-sixth mark volume (marks "4", "5", and "6"). Additionally, volume definition circuitry 960 has automatically generated a recommended volume (or "hint", represented by a dash-line contour in FIG. 15) based on one or more test volumes for which the corresponding one or more clinical effect sets have been determined. In various embodiments, the target volume results from building up a volume from successive clinical effects mappings based on multiple test volumes. In the illustrated example, a guidance button ("Guidance?") allows the user to request a recommended that recommends or suggests a search direction or stimulation configuration, which as shown in FIG. 15 is displayed in volume definition panel 1064 in a perspective view.

In various embodiments, after a certain number of test volumes have been assessed (using the corresponding clinical effects), and/or if the search mode is selected, the algorithm can provide a recommended volume. Volume definition circuitry 960 may provide an option and display it in volume definition panel 1064 to allow the user to specify a floor of the clinical effects (e.g., one or one set of minimum scores and/or parameters) and/or a target magnitude of the clinical effects (e.g., one or one set of targeted scores and/or parameters) to be represented by the recommended volume. Such floor and target parameters and/or other one or more threshold parameters associated with the recommended volume can also be programmed (e.g., hard-coded) into a neurostimulator. A stimulation configuration providing for a volume of activation that substantially matches the recommended volume can then be determined.

In various embodiments, user interface 910 can allow the user to mark volumes and/or control points to track the progression of clinical mapping. The control points can include the center of a library-generated volume to be saved, the exact point at which the user clicked to define a volume, or another reasonable approximation of stimulation (e.g., central point of a "template" volume, or centroid of a calculated volume) that can be compartmentalized into a single point. Marks may be representative of the sequence of test volumes attempted (e.g., marks "1"-"6" as shown in FIG. 15), representative of the net clinical effect achieved (e.g. colored/filled circles), and/or indicative of particularly favorable or unfavorable control points. A volume associated with a mark can be referred to as a "mark volume" in this document. The user interface can also allow the user to score each mark in a similar fashion as a test volume is scored. Marks can also be shaded or otherwise represented according to how recently they were placed (e.g. numbers as shown in FIGS. 11-15, or gray scales with black indicating the earliest and white indicating the latest) with respect to order and/or chronological time).

In various embodiments, volume definition circuitry 960 can determine the target volume based on the one or more test volumes, the recommended volume(s), and/or the mark volume(s). For example, volume definition circuitry 960 can allow the user to set the target volume to an effective volume. The effective volume can be a test volume selected by the user using the one or more clinical effects associated with that test volume. The user can set the target volume to the effective volume by selecting the effective volume and hitting the "SET" button. Volume definition circuitry 960 can also allow the user to set the target volume to the recommended volume, and/or can also allow the user to set the target volume to a mark volume. The user can specify a mark for the associated mark volume to be used as the target volume. The stimulation configuration saved with the specified mark is used as the stimulation configuration used for programming the neurostimulator. Mark can be accessed from the main perspective view, a specific mark view, a menu slider, or any other suitable user interface representations. In various embodiments, volume definition circuitry 960 can also allow the user to set the target volume to any of the assessed test volume(s), recommended volume(s), and mark volume(s). Stimulation configuration circuitry 962 generates the stimulation configuration for that target volume, and programming control circuit 816 generates the plurality of stimulation parameters for programming the stimulation device based on the stimulation configuration. In various embodiments, volume definition circuitry 960 can display a message using presentation device 856 to require the user to confirm the target volume before it is used for programming the stimulation device.

FIGS. 16-28 each illustrate an example of a presentation of a target volume and clinical effects on user interface 910.

In various embodiments, volume definition circuitry 960 can graphically present the clinical effects and the various volumes discussed in this document in various views using presentation device 856, such as on the display screen of presentation device 856.

Figure 16:
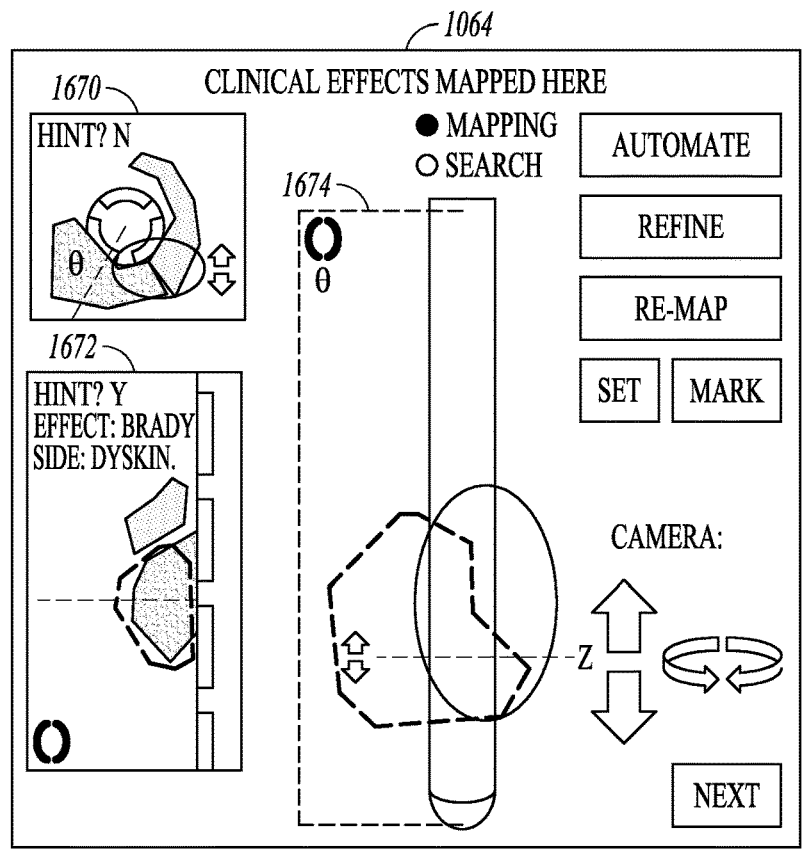
FIG. 16 illustrates an example of a presentation related to a target volume and clinical effects on a user interface, such as the user interface of FIG. 9.

FIG. 16 illustrates an example of a presentation related to a target volume and clinical effects on a volume definition panel 1664 on the display screen. The target volume and the clinical effects are presented in an overall or perspective view 1674 and cross-sectional views 1670 and 1672. The target volume, including the various volumes used to determine the target value (i.e., the one or more test volumes, recommended volumes, and mark volumes) are independent of the lead being used or the stimulation configuration to be generated. In other words, specific information of the lead is used only after the target volume has been determined and the stimulation configuration is to be determined. Volume definition circuitry 960 can present on the display screen cross-sectional and/or other profile views of the lead, electrodes on the lead, and volumes (e.g., the one or more test volumes, recommended volumes, and mark volumes), and allow the user to choose the cross-section (z in FIG. 16) and the viewing angel (θ in FIG. 16). In the illustrated example, volume definition circuitry 960 allows the user to choose the cross-section plane (z in FIG. 16) using the up-down arrows and the perspective angel (θ in FIG. 16) using the rotation arrows. The user can toggle between choosing the cross-section plane and choosing the perspective angle on the user interface. In the illustrated example, indicators for the cross-sectional plane (z line) and the perspective angle (θ line) are presented with the lead profile. In various embodiments, such indicators may not be necessary while the user is provided with means to choose the cross-section plane and the perspective angle.

Figure 17:
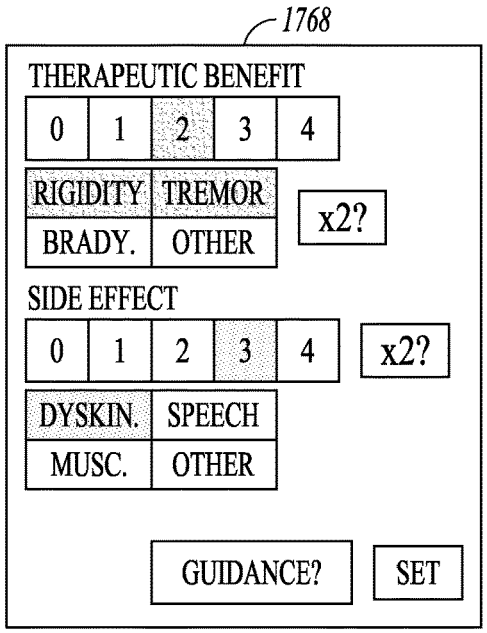
FIG. 17 illustrates an example of a presentation of a clinical effects console on a user interface, such as the user interface of FIG. 9.

In the illustrated example, a recommended volume and a current test volume, or the recommended volume and a current stimulation volume, are shown in volume definition panel 1664. Volumes can also be shown along with series of prior marks. The rotation arrows allow the user to swipe through various perspective angles (θ). The up-down arrows allow user to specify each cross-sectional plane (z), or the user can specify each cross-sectional plane by drag/drop. Cross-sectional views can be independent of the overall view and switchable with the clinical effects console (FIG. 17). In one embodiment, volume definition circuitry 960 allows the user to select whether to show the recommended volume in each cross-sectional view (e.g., not shown in cross-sectional view 1670, but shown in cross-sectional view 1672, as illustrated in FIG. 16). In various embodiments, cross-sectional views show single "slices" (e.g., z as shown in FIG. 16) that represent total clinical effects volume (s). These cross-sections can flip with cross-section controls and update with clinical entries (see FIG. 17). In various embodiments, volume definition circuitry 960 allows the user to switch between clinical effects (e.g., one or more therapeutic benefits and one or more side effects) regarding specific symptoms.

FIG. 17 illustrates an example of a presentation of a clinical effects console 1768 on the display screen. In various embodiments, the clinical effects (e.g., one or more therapeutic benefits and one or more side effects) can be presented in a form of menus of symptoms shown as sliders and/or have additional weighting options. In various embodiments, selectable weights can be applied to the symptoms in calculating a composite therapeutic benefit or side effect score. In the illustrated example, a "Guidance?" button allows the user to obtain a recommended volume under the manual mode, and a "SET" button displayed next to the Guidance button allows the user to set the target volume to the recommended volume.

FIG. 18-20 each illustrate an example of cross-sectional views 1670 and 1672 of the target volumes and the clinical effects. In various embodiments, volumes, recommended volumes, and marks are all independent of the lead being used or the stimulation parameters being programmed into the stimulation device. Various colors and/or scaled colors can be used to distinctly indicate various effects such as composite therapeutic benefits, individual therapeutic benefits (e.g., each for a specific symptom), composite side effects, individual side effects (e.g., each for a specific side effect), and/or can be used to distinctly indicate order of the volumes assessed. The user can select between whether to present each volume (e.g., each of the test, recommended volume, and mark volumes) in each of cross-sectional views 1670 and 1672. In various embodiments, a cross-sectional view may include internal interpolated surface cuts/profiles (e.g., FIG. 18), may show only the contour of each clinical effects volume (e.g., FIG. 19), or may show volumes or contours representing clinical effects associated with the current and preceding assessment of test volumes (e.g., FIG. 20).

FIGS. 21 and 22 each illustrate an example of perspective view 1674 of the target volumes and the clinical effects. In various embodiments, volumes, recommended volumes, and marks are all independent of the lead being used or the stimulation parameters being programmed into the stimulation device. Various colors and/or scaled colors can be used to distinctly indicate various effects such as composite therapeutic benefits, individual therapeutic benefits (e.g., each for a specific symptom), composite side effects, individual side effects (e.g., each for a specific side effect), and/or can be used to distinctly indicate order of the volumes assessed. In various embodiments, perspective view 1674 can show a current volume and a recommended volume (e.g., FIG. 21), or can show assessed test volumes and a recommended volume, with the test volumes marked with color or other distinctive feature indicating their corresponding clinical effects and/or chronological order of their assessment (e.g., FIG. 22).

Figure 23:
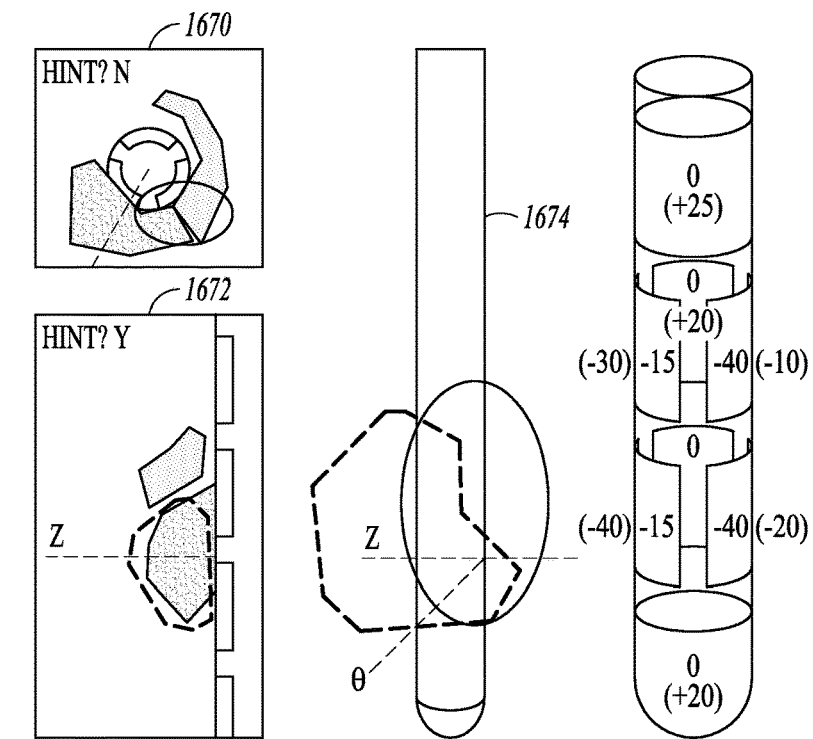
FIG. 23 illustrates an example of presenting a recommended volume and clinical effects on a user interface, such as the user interface of FIG. 9.
Figure 24:
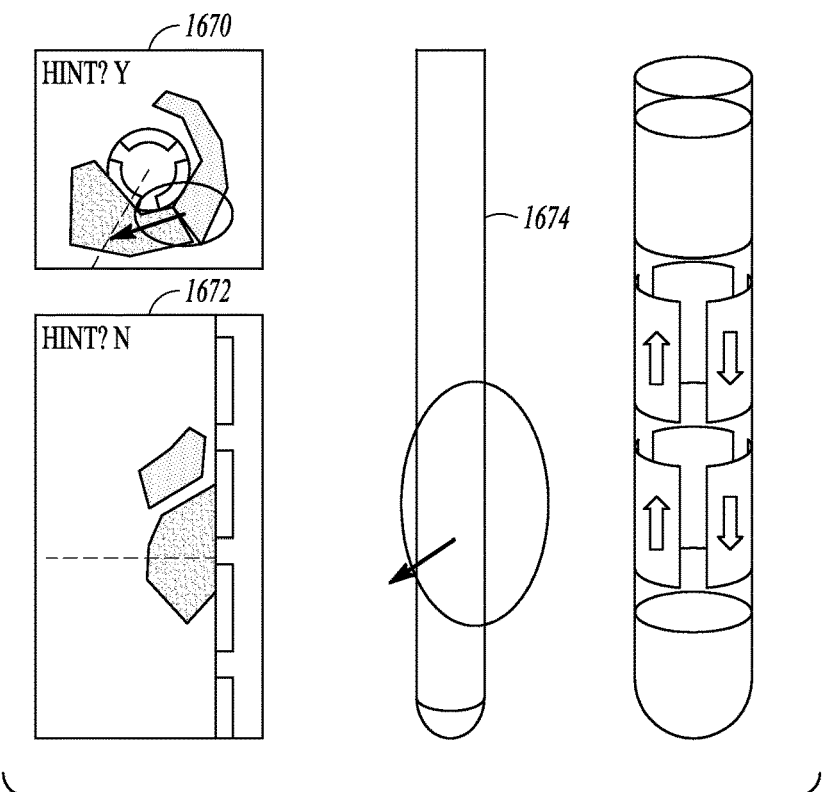
FIG. 24 illustrates another example of presenting a recommended volume and clinical effects on a user interface, such as the user interface of FIG. 9.

FIGS. 23-25 each illustrate an example of presenting a recommended volume with corresponding clinical effects as shown in cross-sectional views 1670 and 1672 and/or perspective view 1674. In various embodiments, once a region of tissue is sufficiently mapped (e.g. after a certain number of test volumes are assessed) and/or when the search mode is selected, volume definition circuitry 960 can generate a recommended volume. In one embodiment, such as illustrated in FIG. 23, a recommended volume is displayed as an explicit volumes and cross-sections, with the fractionalization shown on a lead with electrodes (e.g., using colors to associate each volume with a corresponding stimulation configuration). Exact stimulation configuration used to generate the recommended volume may or may not be shown to user, and user may or may not be able to choose whether to show it. In another embodiment, such as illustrated in FIG. 24, a recommended is displayed (by e.g. arrows, symbols, or other indicators) to suggest directions of change in volume (and corresponding stimulation configuration) and general trends, to enable the user to apply discretion on increments taken for the test volumes. Such direction can be derived from, for example, logical comparisons between current stimulation configuration and clinical-effects-based volumes, or difference between current stimulation configuration and shape defining points of the test volumes (e.g., center of mass, foci, or vertices). In another embodiment, such as illustrated in FIG. 25, recommended volumes can be integrated with marks and/or a concurrent closed-loop optimization algorithm, and can represent a recommended next step and/or a recommended first step of closed-loop search should it be initiated from the current site.

FIGS. 26-28 each illustrate an example of presenting a mark with corresponding clinical effects as shown in cross-sectional views 1670 and 1672 and/or perspective view 1674. In various embodiments, marks may or may not be shown on an overall perspective view. Marks can be numbers, dots, stars, and/or other symbols. Marks (as symbols rather than volumes or contours) can be colored corresponding to the clinical effects (therapeutic benefits and/or side effects). Direction or progression of marking (e.g., chronological order of the marks) may or may not be shown. All the marks, or only those centered on a selected cross-section, may be shown with each cross-sectional view. Marks may be recorded and stored with corresponding clinical notes, and/or be named (e.g., "Brady 3") and stored with corresponding clinical effects scores and/or stimulation configurations. A currently selected mark and the corresponding cross-section can be denoted by size, color, or another distinguishing feature. In one embodiment, such as illustrated in FIG. 26, marks (numbers) denote the order of control points assessed during the process of determining the target volume. Marks can also be circles that are shaded according to how recently the location was assessed. In another embodiment, such as illustrated in FIG. 27, the user can save the marks (together with the corresponding stimulation configuration) for reference and potential later use. Marks can be denoted as being saved (e.g., by circles) with marker shading or attribute (e.g., font, size, or symbol) denoting how effective the mark volume is (e.g., based on the clinical effects score), how recently mark was established, and/or other attribute(s). In another embodiment, such as illustrated in FIG. 28, marks can be placed (e.g. by clicking on a cross-section, the "Mark" button on the user interface, and/or selected using a grid such as intersection points) and maneuvered using directional controls. Grid resolution may be controlled with, for example, a set of buttons, or a slider.

Figure 29:
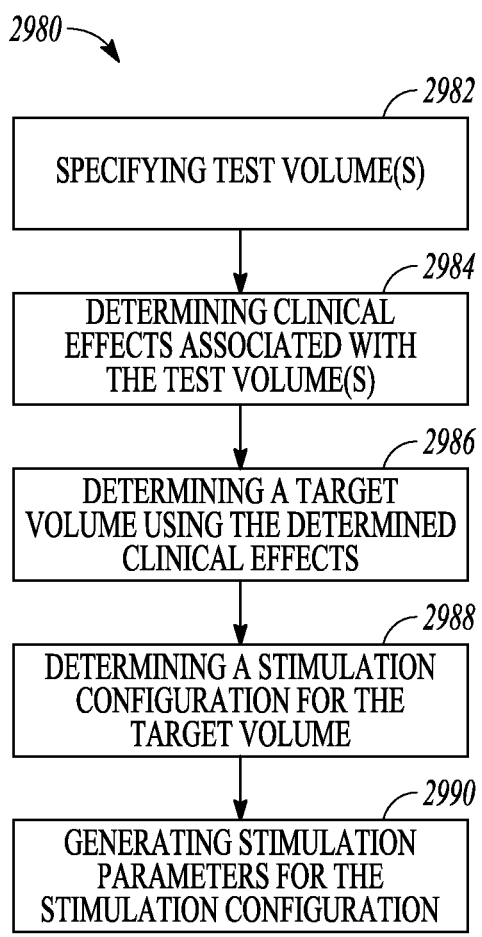
FIG. 29 illustrates an embodiment of a method for programming neurostimulation using clinical effects.

FIG. 29 illustrates an embodiment of a method 2980 for programming neurostimulation using clinical effects. In one embodiment, system 100, including its various embodiments discussed in this document, is used to perform method 2980. For example, a programming device such as external programming device 802 can be configured to perform method 2980.

At 2982, one or more test volumes are specified. The one or more test volumes each represent a portion of tissue in a patient to whom the neurostimulation is to be delivered. In one embodiment, the user is allowed to specify a stimulation configuration to be tested, and a corresponding test volume is automatically generated by executing a modeling algorithm that is based on, for example, SFM. In another embodiment, the user is allowed to specify the test volume directly, and the corresponding stimulation configuration is automatically generated by executing an inverse modeling algorithm that is based on, for example, SFM. In various embodiments, the user can be allowed to specify the test volume directly and/or by specifying the corresponding stimulation configuration. The test volume is to be activated by delivery of the neurostimulation using the corresponding stimulation configuration. In various embodiments, the test volume and the corresponding stimulation configuration can be presented to the user, such as on a display screen of the programming device.

At 2984, clinical effects associated with the one or more test volumes are determined. For each specified test volume, the neurostimulation can be delivered according to the corresponding stimulation configuration, and the clinic effects associated with the test volume can be determined based on manually entered information and/or signals sensed from the patient. The manually entered information can include observations by the user and/or feedback provided by the patient. In various embodiments, a clinical effect information set can be generated to represent the determined clinical effects, and presented on the display screen. The clinical effect information set can include various types and degrees of one or more therapeutic benefits and one or more side effects associated with the test volumes and the recommended volume can be determined and presented on the display screen. Examples of clinical effects information display include an overall therapeutic benefit score, one or more therapeutic benefit types, a therapeutic benefit score for each of the one or more therapeutic benefit types, an overall side score, one or more side effect types, a side effect score for each of the one or more side effect types, a therapeutic benefits contour, and/or a side effect contour. The therapeutic benefits contour is indicative of a volume of the tissue excitable for one or more desirable therapeutic benefits. The side effect contour is indicative of a volume of the tissue excitable for one or more unwanted side effects.

At 2986, a target volume is determined using at least the clinical effects determined at 2984. The target volume can be the volume of activation corresponding to an optimal stimulation configuration, and can be determined by targeting at maximizing the one or more therapeutic benefits while minimizing the one or more side effects. In various embodiments, the target volume can be determined as an optimal balance of the one or more therapeutic benefits and the one or more side effects. In various embodiments, the target volume is determined via an iterative process that repeats steps 2982, 2984, and 2986. For example, each iteration of the iterative process can include defining a test stimulation configurations representing an attempt to defining the target volume, determining the test volume corresponding to the test stimulation configuration, and determining the clinical effect information set representing the clinic effects associated with the test volume. When the clinical effects are assessed for sufficient number of test volumes, the target volume can be determined using the test volumes and their associated clinical effect information sets. The iterative process can further include allowing a user to mark a test volume as a mark volume to allow for tracking of the attempts to define the target volume. In various embodiments, the iterative process can further include automatically generating a recommended volume based on the test volumes and their associated clinical effect information sets. In various embodiments, the user can set the target volume to the mark volume, the recommended volume, or a test volume of the test volumes. In various embodiments, one or more of the target volume, the mark volume, the recommended volume, the test volumes, or one or more graphical representation of the clinical effect information sets are presented on the display screen in one or more of a cross-sectional view at a cross-section selected by the user or a perspective view at a perspective angle selected by the user. A graphical representation of the stimulation configuration can also be presented on the display screen.

At 2988, a stimulation configuration is determined for the target volume. The inverse modeling algorithm can be used to automatically generate the stimulation configuration according to which the neurostimulation is to be delivered to stimulate the target volume (a portion of tissue of the patient). In various embodiments, the inverse modeling algorithm can generate a stimulation configuration for activating a volume of tissue in the patient that substantially matches the target volume, such that the intended clinical effects can be expected when the neurostimulation is delivered according to the stimulation configuration. In various embodiments, the stimulation configuration can include an electrode configuration specifying a selection of the one or more electrodes from a plurality of electrodes and a fractionalization of electrical current flowing through the selected one or more electrodes. In various embodiments, the stimulation configuration can be generated automatically using a library including data mapping volumes of activation to stimulation configurations, and/or generated automatically using an analytical derivation of the stimulation configuration from the stimulation volume.

At 2990, a plurality of stimulation parameters controlling delivery of the neurostimulation from a stimulation device through one or more electrodes of the plurality of electrodes is generated based on the stimulation configuration that is determined for the target volume. The stimulation device delivers the neurostimulation, such as in the form of electrical pulses, to a patient. In various embodiments, the stimulation device can be used to deliver DBS, SCS, PNS, VNS, and any other types of neurostimulation.

In various embodiments, a volume (including any volume used in method 2980) can be defined by r, z points on θ-planes, or by explicit or interpolated x, y points on z-planes. Data are represented as matrices whose values are entered by user-specified clinical effects (e.g., equally or unequally weighted therapeutic benefit and side effect entries), and can also be converted into contours (thresholds), levels, or booleans, and displayed on cross-sections. These contours, levels, or booleans can be used for point-by-point or sum distance comparisons. The clinical effects threshold can be built into the stimulation device to be programmed or specified by the user using the user interface. A recommended volume represents a volume in a device library and/or a volume derived from analytical calculation/approximation which best matches a potential target volume (e.g., defined by the threshold of therapeutic benefits). This volume can be encoded and segmented (e.g. by rz on θ planes or xy on z-planes, similar to the clinical effects volumes. Distance D between the target volume (set to a recommended volume, a mark volume, or test volume) and the stimulation volume (selected from the library) to be minimized between derived and potential target volumes for the purpose of finding and showing the recommended volume can be expressed as a total or weighted Hamming distance, a total or weighted spatial distance, a distance between edge or contour points along rows and columns, or a similar metric.

In various embodiments, the stimulation configuration can be determined based on the target volume by "rounding" to nearest steering state based on centroid coordinate entry, rounding to the nearest SFM for a lead with electrodes, and searching for best primitive (and associated fractionalization) based on minimized Hamming differences between features of target and library SFMs (e.g. volume, edge contours, and profiles on specific angle planes).

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation from a stimulation device to tissue of a patient through a plurality of electrodes, the system comprising:
   a programming control circuit configured to generate information for programming the stimulation device to control delivery of the neurostimulation according to a stimulation configuration defining one or more stimulation waveforms and one or more electrode configurations; and
   a stimulation control circuit configured to determine the stimulation configuration, the stimulation control circuit including:
   volume definition circuitry configured to determine one or more test volumes, to determine one or more clinical effects each resulting from a test volume of the one or more test volumes being activated by the neurostimulation, and to determine a target volume using the one or more test volumes and the one or more clinical effects; and
   stimulation configuration circuitry configured to automatically generate the specified stimulation configuration for activating a stimulation volume substantially matching the target volume by executing an inverse modeling algorithm using a stimulation field model (SFM) relating the stimulation configuration to the stimulation volume and at least one of a library including data mapping volumes of activation to stimulation configurations or an analytical derivation of the stimulation configuration that generates the stimulation volume,
   wherein the one or more test volumes, the target volume, and the stimulation volume each represent a portion of the tissue.

2. The system of claim 1, wherein the stimulation configuration circuitry is further configured to determine the stimulation configuration by minimizing a difference between the stimulation volume and the target volume.

3. The system of claim 2, wherein the stimulation configuration circuitry is further configured to determine the stimulation configuration by minimizing a Hamming distance between the stimulation volume and the target volume, a spatial distance between the stimulation volume and the target volume, or a distance between edge or contour points of the stimulation volume and the target volume.

4. The system of claim 1, comprising a user interface including a display screen, a user input device, and the stimulation control circuit, and wherein the volume definition circuitry is further configured to present a graphical representation of a volume of the one or more test volumes and the target volume in a volume panel on the display screen and to present a graphical representation of a stimulation configuration corresponding to the presented volume in a stimulation configuration panel on the display screen.

5. The system of claim 4, wherein the volume definition circuitry is further configured to present the graphical representation of the volume in at least a cross-sectional view at a user-selected cross-section received using the user input device or a perspective view at a user-selected perspective angle received using the user input device.

6. The system of claim 1, wherein the stimulation control circuit is configured to determine each electrode configuration of the one or more electrode configurations by specifying a selection of one or more electrodes from the plurality of electrodes and a fractionalization of electrical current flowing through the selected one or more electrodes.

7. The system of claim 1, wherein the stimulation configuration circuitry is further configured to generate a recommendation for a direction for determining the target volume using the one or more test volumes, the one or more clinical effects, and one or more threshold parameters and to determine the target volume using the recommendation.

8. The system of claim 7, wherein the volume definition circuitry is further configured to:
determine clinical effect information sets each representing a clinical effect of the one or more clinical effects and each including a measure of a therapeutic benefit and a measure of a side effect; and
determine the recommendation using the one or more test volumes, the clinical effect information sets, and the one or more threshold parameters.

9. A method for delivering neurostimulation from a stimulation device to tissue of a patient through a plurality of electrodes, the system comprising:
determining one or more test volumes using a processor;
determining one or more clinical effects each resulting from a test volume of the one or more test volumes being activated by the neurostimulation using the processor;
determine a target volume using the one or more test volume and the one or more clinical effects using the processor;
automatically generating a stimulation configuration defining one or more stimulation waveforms and one or more electrode configurations, using the processor, for activating a stimulation volume substantially matching the target volume by executing an inverse modeling algorithm using a stimulation field model (SFM) relating the stimulation configuration to the stimulation volume and at least one of a library including data mapping volumes of activation to stimulation configurations or an analytical derivation of the stimulation configuration that generates the stimulation volume; and
generating information for programming the stimulation device to control the delivery of the neurostimulation according to the stimulation configuration using the processor,
wherein the one or more test volumes, the target volume, and the stimulation volume each represent a portion of the tissue.

10. The method of claim 9, wherein automatically generating the stimulation configuration comprises determining the stimulation configuration by minimizing a difference between the stimulation volume and the target volume.

11. The method of claim 10, wherein minimizing the difference between the stimulation volume and the target volume comprises minimizing a Hamming distance between the stimulation volume and the target volume.

12. The method of claim 10, wherein minimizing the difference between the stimulation volume and the target volume comprises minimizing a spatial distance between the stimulation volume and the target volume.

13. The method of claim 10, wherein minimizing the difference between the stimulation volume and the target volume comprises minimizing a distance between edge or contour points of the stimulation volume and the target volume.

14. The method of claim 9, further comprising:
presenting a graphical representation of a volume of the one or more test volumes and the target volume on a display screen of a user interface; and
presenting a graphical representation of a stimulation configuration corresponding to the presented volume on the display screen.

15. The method of claim 14, further comprising presenting the graphical representation of the volume in at least a cross-sectional view at a user-selected cross-section received by the user interface or a perspective view at a user-selected perspective angle received by the user interface.

16. The method of claim 9, wherein automatically generating the stimulation configuration comprises determining, for each electrode configuration of the one or more electrode configurations, a selection of one or more electrodes from the plurality of electrodes and a fractionalization of electrical current flowing through the selected one or more electrodes.

17. The method of claim 9, wherein determining the one or more clinical effects comprises determining one or more therapeutic benefits and one or more side effects.

18. A non-transitory computer-readable storage medium including instructions, which when executed by a system, cause the system to perform a method for controlling delivery of neurostimulation to tissue of a patient, the method comprising:
determining one or more test volumes;
determine one or more clinical effects each resulting from a test volume of the one or more test volumes being activated by the neurostimulation;
determine a target volume using the one or more test volume and the one or more clinical effects;
automatically generating a stimulation configuration defining one or more stimulation waveforms and one or more electrode configurations for activating a stimulation volume substantially matching the target volume by executing an inverse modeling algorithm using a stimulation field model (SFM) relating the stimulation configuration to the stimulation volume and at least one of a library including data mapping volumes of activation to stimulation configurations or an analytical derivation of the stimulation configuration that generates the stimulation volume; and
generating information for programming the stimulation device to control the delivery of the neurostimulation according to the stimulation configuration,
wherein the one or more test volumes, the target volume, and the stimulation volume each represent a portion of the tissue.

19. The non-transitory computer-readable storage medium of claim 18, wherein automatically generating the stimulation configuration comprises determining the stimulation configuration by minimizing a difference between the stimulation volume and the target volume.

20. The non-transitory computer-readable storage medium of claim 18, wherein automatically generating the stimulation configuration comprises determining, for each electrode configuration of the one or more electrode configurations, a selection of one or more electrodes from the plurality of electrodes and a fractionalization of electrical current flowing through the selected one or more electrodes.

* * * * *